(12) United States Patent
Liphardt et al.

(10) Patent No.: US 7,215,423 B1
(45) Date of Patent: May 8, 2007

(54) CONTROL OF BEAM SPOT SIZE IN ELLIPSOMETER AND THE LIKE SYSTEMS

(75) Inventors: Martin M. Liphardt, Lincoln, NE (US); Blaine D. Johs, Lincoln, NE (US); John A. Woollam, Lincoln, NE (US); James D. Welch, Omaha, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 415 days.

(21) Appl. No.: 10/963,402

(22) Filed: Oct. 10, 2004

Related U.S. Application Data

(63) Continuation-in-part of application No. 10/829,620, filed on Apr. 22, 2004, and a continuation-in-part of application No. 10/426,590, filed on Apr. 30, 2003, now Pat. No. 7,057,717, and a continuation-in-part of application No. 09/583,229, filed on May 30, 2000, now Pat. No. 6,804,004, and a continuation-in-part of application No. 09/496,011, filed on Feb. 1, 2000, now Pat. No. 6,353,477, and a continuation-in-part of application No. 09/419,794, filed on Oct. 18, 1999, now Pat. No. 6,549,282.

(60) Provisional application No. 60/512,446, filed on Oct. 20, 2003, provisional application No. 60/527,554, filed on Dec. 6, 2003, provisional application No. 60/527,638, filed on Dec. 8, 2003, provisional application No. 60/405,858, filed on Aug. 26, 2002.

(51) Int. Cl.
*G01J 4/00* (2006.01)

(52) U.S. Cl. .................................................. 356/369
(58) Field of Classification Search ................ None
See application file for complete search history.

(56) References Cited

U.S. PATENT DOCUMENTS

| | | | | |
|---|---|---|---|---|
| 4,636,075 | A | 1/1987 | Kollenberg | 356/336 |
| 4,668,860 | A | 5/1987 | Anthon | 250/225 |
| 4,893,932 | A | 1/1990 | Kollenberg | 356/369 |
| 5,166,752 | A | 11/1992 | Spanier et al. | 356/369 |
| 5,333,052 | A | 7/1994 | Finarov | 356/369 |
| 5,596,406 | A | 1/1997 | Rosencwaig et al. | 356/327 |
| 5,608,526 | A | 3/1997 | Piwonka-Corle et al. | 356/369 |
| 5,633,747 | A * | 5/1997 | Nikoonahad | 359/312 |
| 5,793,480 | A | 8/1998 | Lacey et al. | 356/73 |
| 5,798,837 | A | 8/1998 | Aspnes et al. | 356/369 |
| 5,877,859 | A | 3/1999 | Aspnes et al. | 356/364 |
| 5,917,594 | A | 6/1999 | Norton | 356/327 |
| 5,936,734 | A | 8/1999 | Johs et al. | 356/364 |
| 6,248,988 | B1 * | 6/2001 | Krantz | 250/201.3 |
| 6,493,097 | B1 | 12/2002 | Ivarsson | 356/630 |
| 2002/0163634 | A1 | 11/2002 | Meeks | |

* cited by examiner

*Primary Examiner*—Tu T. Nguyen
(74) *Attorney, Agent, or Firm*—James D. Welch

(57) ABSTRACT

System and methodology for controlling a beam spot size where it impinges onto a sample, and/or discriminant selection and analysis of data from detector elements in a two dimensional detector array which correspond to identified regions on a sample.

29 Claims, 10 Drawing Sheets

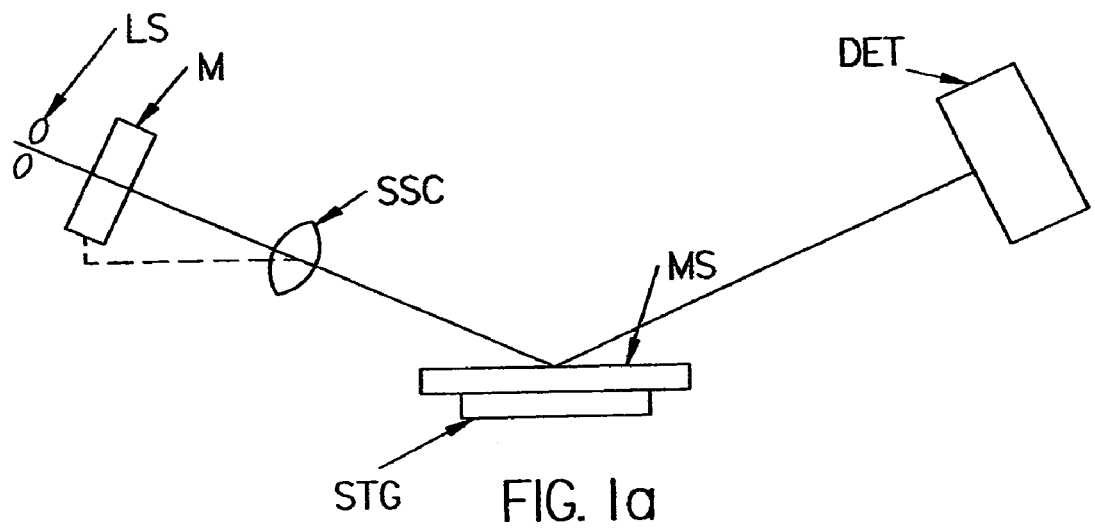
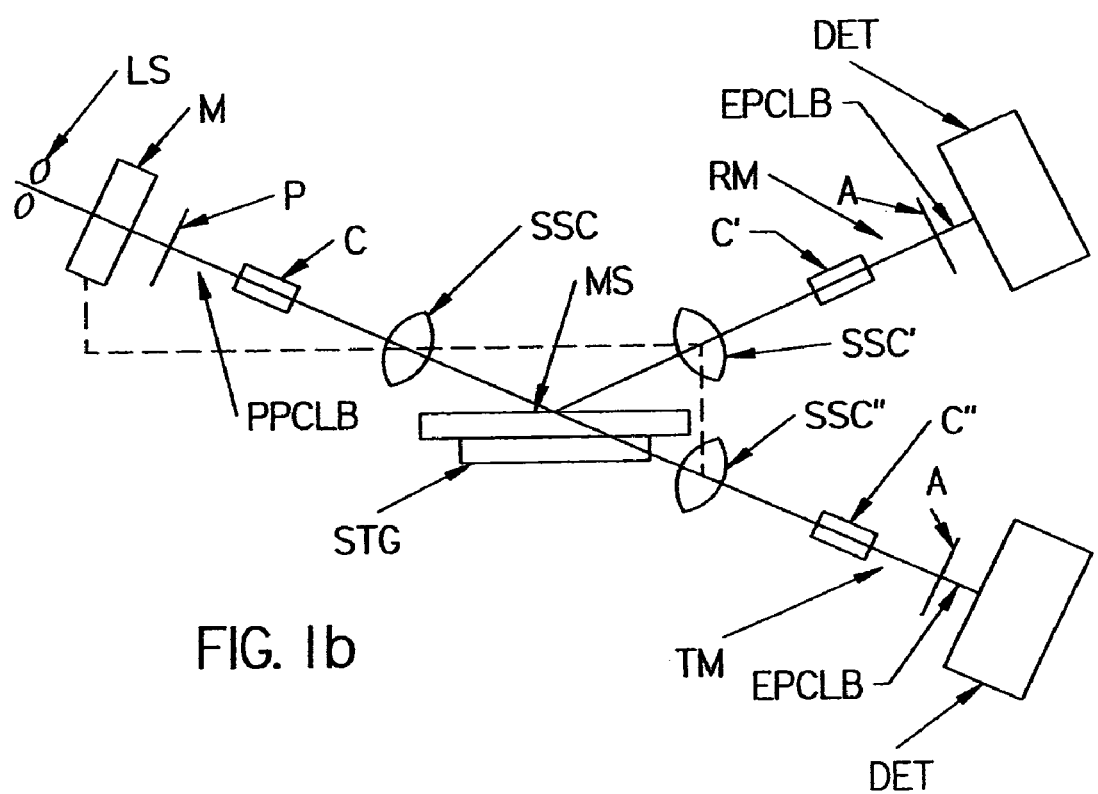

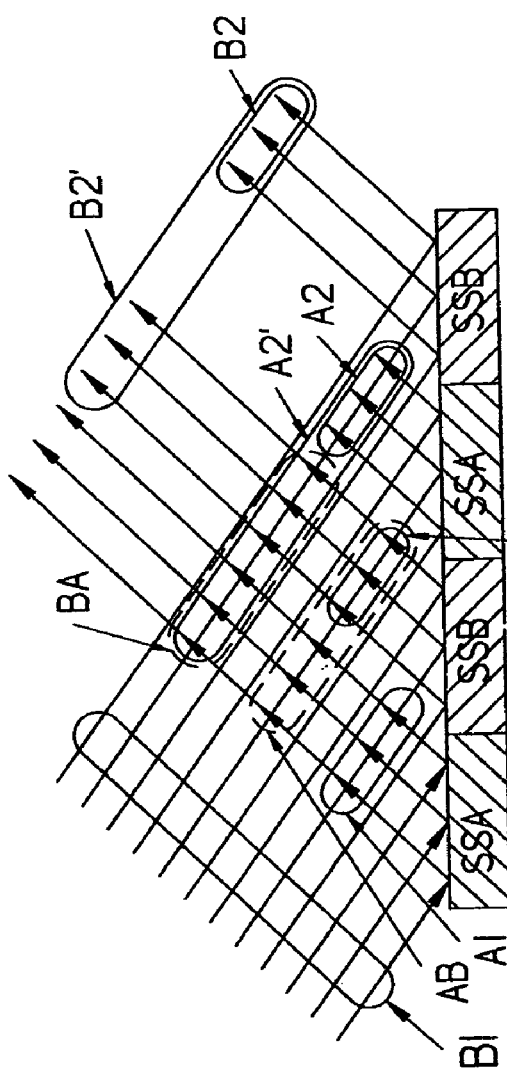
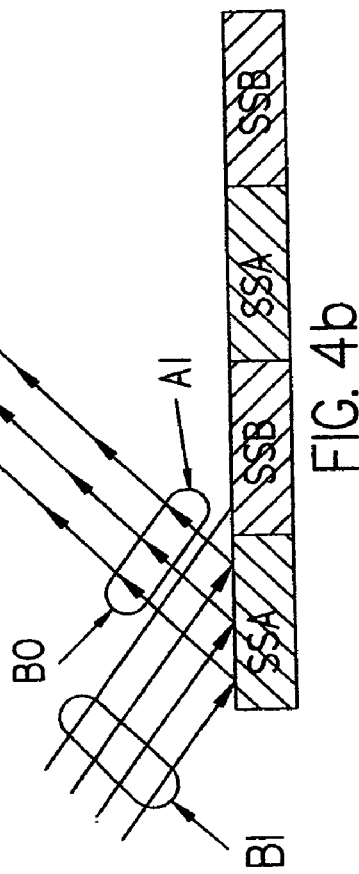

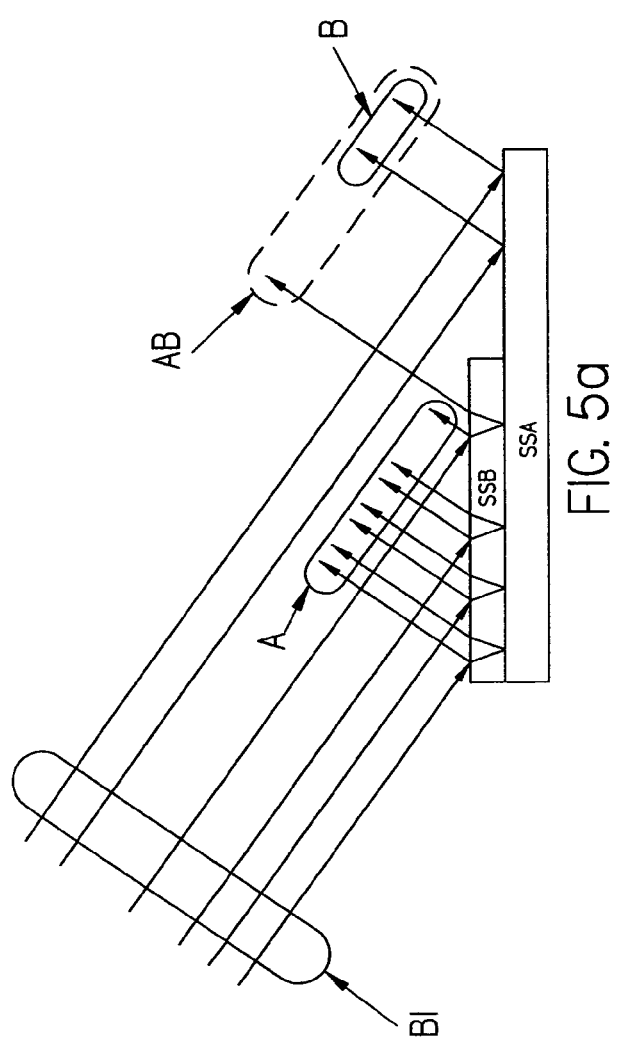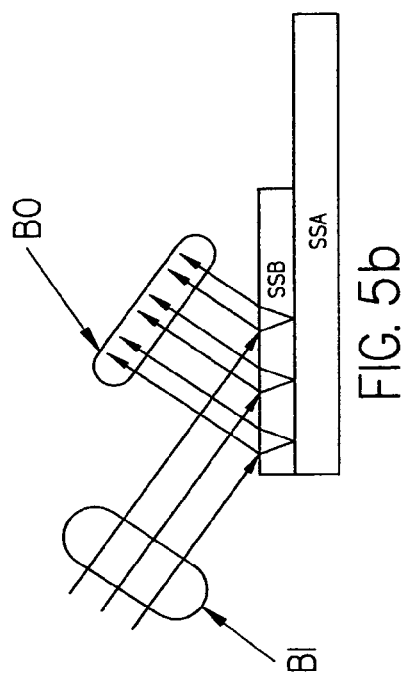
FIG. 5a
FIG. 5b

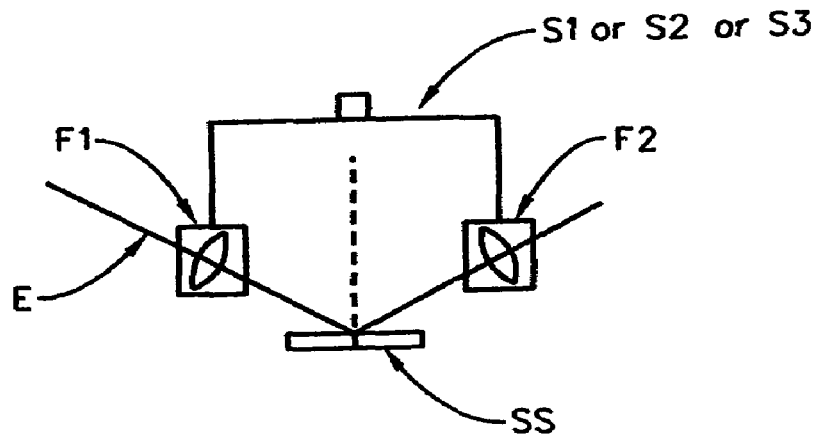
FIG. 6a1
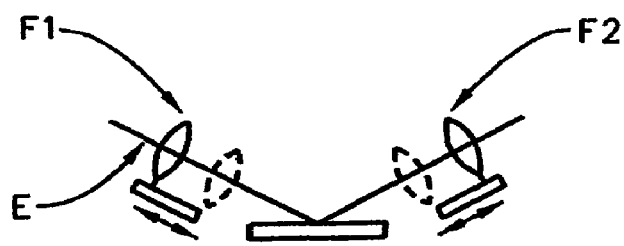
FIG. 6a2
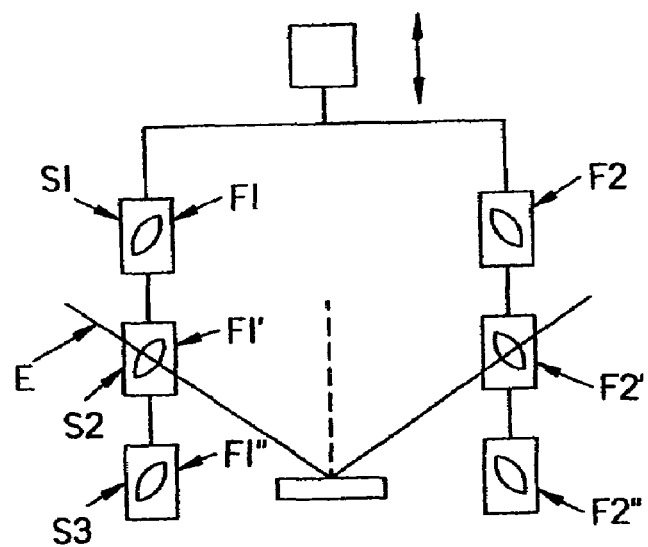
FIG. 6a3

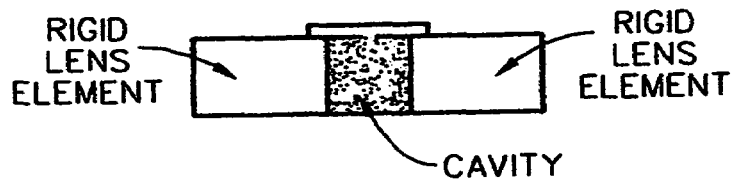
FIG. 8a
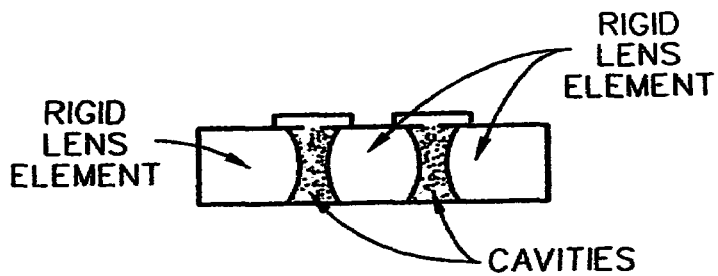
FIG. 8b
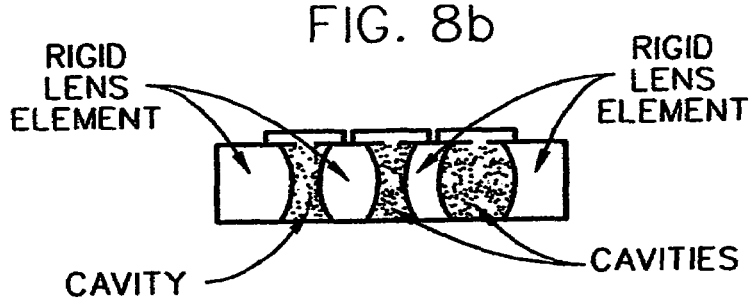
FIG. 8c
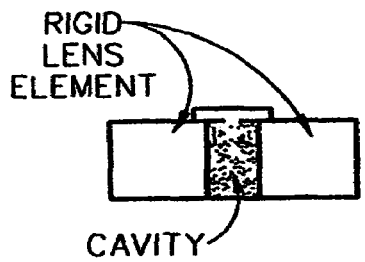 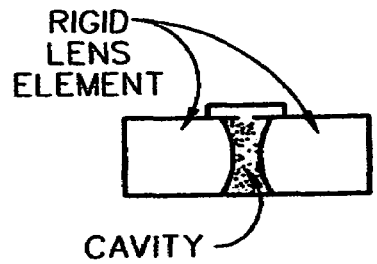 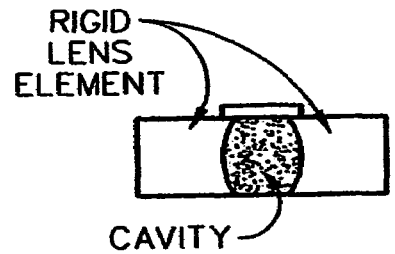
FIG. 8d     FIG. 8e     FIG. 8f
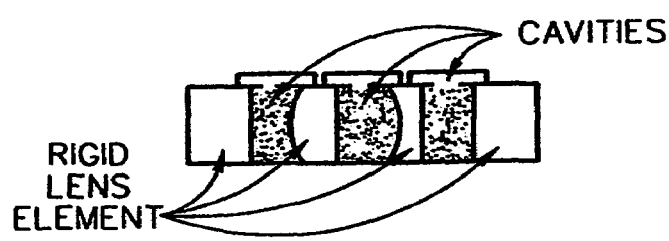
FIG. 8g

CONTROL OF BEAM SPOT SIZE IN ELLIPSOMETER AND THE LIKE SYSTEMS

This Application is a CIP of application Ser. No. 10/426,590 Filed Apr. 30, 2003, (now U.S. Pat. No. 7,057,717), and therevia Claims benefit of Provisional Application Ser. No. 60/405,858 Filed Aug. 26, 2002. This Application directly and Claims benefit of Provisional Application Ser. No. 60/512,446 Filed Oct. 20, 2003. Further this Application is a CIP of Allowed application Ser. No. 09/583,229, Filed May 30, 2000, (now U.S. Pat. No. 6,804,004), and therevia of application Ser. No. 09/419,794 Filed Oct. 18, 1999, (now U.S. Pat. No. 6,549,282), and of application Ser. No. 09/496,011 Filed Feb. 1, 2000, (now U.S. Pat. No. 6,353,477). This Application is further Claims benefit of Provisional 60/512,446 Filed Oct. 20, 2003, and of Provisionals 60/527,554 Filed Dec. 6, 2003 and 60/527,638 Filed Dec. 8, 2003. This Application is further a CIP of Pending application Ser. No. 10/829,620 Filed Apr. 22, 2004.

TECHNICAL FIELD

The disclosed invention relates to methodology for investigating samples with electromagnetic beams, and more particularly to systems and methodology which involves control of a beam spot size where it impinges onto a sample, and/or discriminant selection and analysis of data from detector elements in a multi-dimensional detector array, which correspond to identified regions on a sample.

BACKGROUND

The practice of ellipsometry is well established as a non-destructive approach to determining characteristics of material systems, and can be applied in real time process control. The topic is generally well described in a number of publication, one such publication being a review paper by Collins, titled "Automatic Rotating Element Ellipsometers: Calibration, Operation and Real-Time Applications", Rev. Sci. Instrum, 61(8) (1990).

In general, modern practice of ellipsometry typically involves causing a spectroscopic beam of electromagnetic radiation, in an imposed, known, state of polarization, to interact with a material system at one or more angle(s) of incidence with respect to a normal to a surface thereof, in a plane of incidence. (Note, a plane of incidence contains both a normal to a surface of an investigated material system and the locus of said beam of electromagnetic radiation). Changes in the polarization state of said beam of electromagnetic radiation which occur as a result of said interaction with said material system are indicative of the structure and composition of said material system. The practice of ellipsometry utilizes said changes in polarization state by proposing a mathematical model of the ellipsometer system and the material system investigated by use thereof, obtaining experimental data by application of the ellipsometer system, and applying square error reducing mathematical techniques (eg. regression), to the end that parameters in the mathematical model which characterize the material system are evaluated so that the obtained experimental data, and values calculated by use of the mathematical model have a "best match" relationship.

A goal in ellipsometry is to obtain, for each wavelength in, and angle of incidence of said beam of electromagnetic radiation caused to interact with a material system, material system characterizing PSI and DELTA values, (where PSI is related to a change in a ratio of magnitudes of orthogonal components rp/rs in said beam of electromagnetic radiation, and wherein DELTA is related to a phase shift entered between said orthogonal components $r_p$ and $r_s$, caused by interaction with said material system;

$$\rho = rp/rs = \text{Tan}(\Psi)\exp(i\Delta)$$

As alluded to, the practice of ellipsometry requires that a mathematical model be derived and provided for a material system and for the ellipsometer system being applied. In that light it must be appreciated that an ellipsometer system which is applied to investigate a material system is, generally, sequentially comprised of:

a. a Source of a beam electromagnetic radiation;
b. a Polarizer element;
c. optionally a compensator element;
d. (additional element(s) such as lens(es), beam directing means, and/or windows such as in vacuum chambers);
e. a material system;
f. (additional element(s) such as lens(es), beam directing means, and/or windows such as in vacuum chambers);
g. optionally a compensator element;
h. an Analyzer element; and
i. a Detector System.

Each of said components b.–i. must be accurately represented by a mathematical model of the ellipsometer system along with a vector which represents a beam of electromagnetic radiation provided from said source of a beam electromagnetic radiation, Identified in a. above)

It is noted that various ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems.

Continuing, as disclosed in Pending application Ser. No. 09/583,229, and U.S. Pat. No. 6,034,777, where an ellipsometer system is applied to investigate a small region of a material system present, it must be appreciated that the beam of electromagnetic radiation can be convergently entered thereto through an input lens, and, optionally, exit via a re-collimating output lens. In effect this adds said input, (and output), lenses as elements in the ellipsometer system as "additional elements", (eg. identified in d. and f. above), which additional elements must be accounted for in the mathematical model. If this is not done, material system representing parameters determined by application of the ellipsometer system and mathematical regression, will have the effects of said input, (and output), lenses at least partially correlated thereinto, much as if the input and, (output lenses), were integrally a part of the material system. Further, while lenses, including multi-element lenses utilized the present invention system in ellipsometric settings are typically relatively less birefringent and chromatically dispersive than are, for instance, electromagnetic beam directing mirror systems, in the case where a multi-element input and/or output optical element(s) demonstrates birefringence, the described approach can further comprise a method of accurately evaluating parameters in parameterized equations in a mathematical model of a system of spatially separated input and output elements, (herein beneficially, demonstratively, identified as lenses), as applied in an ellipsometry or polarimetry setting. Said parameterized equations enable, when parameters therein are properly evaluated, independent calculation of retardation entered by each of said multi-element input lens and said multi-element output lens to, or between, orthogonal components of a beam of electromagnetic radiation caused to pass through said input and output lenses. This provides utility in the form of enabling the breaking of correlation between retardation entered between orthogonal components in a spectroscopic electromagetic beam by input and output lenses and by a material system under investigation. (It is to be understood that at least one of said multi-element input and output lenses in an ellipsometer is often at least somewhat birefringent even though it is quasi-achromatic regarding focal length over a relativley wide wavelength range).

Said Pending application Ser. No. 09/583,229, and U.S. Pat. No. 6,034,777, teach methodology for breaking correlation between retardation effects caused by multi-element input and/or output lenses in an ellipsometer system, and retardation effects caused by an adjacent, otherwise ellipsometrically undistinguishable material system being investigated comprises, in any functional order, the steps of:

a. providing spatially separated input and output optical element (eg. lenses which perform as focusing/defocusing means), at least one of said input output lenses demonstrating birefringence when a beam of electromagnetic radiation is caused to pass therethrough, there being a means for supporting a material system positioned between said input and output lenses;

b. positioning an ellipsometer system source of electromagnetic radiation and an ellipsometer system detector system such that in use a beam of electromagnetic radiation provided by said source of electromagnetic radiation is caused to pass through said input lens, interact with said material system in a plane of incidence thereto, and exit through said output lens and enter said detector system;

c. providing a material system to said means for supporting a material system, the composition of said material system being sufficiently well known so that retardance entered thereby to a polarized beam of electromagnetic radiation of a given wavelength, which is caused to interact with said material system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto, given wavelength;

d. providing a mathematical model for said ellipsometer system and said input and output lenses and said material system, comprising separate parameterized equations for independently calculating retardance entered between orthogonal components of a beam of electromagnetic radiation caused to pass through each of said input and output lenses and interact with said material system in a plane of incidence thereto; such that where parameters in said mathematical model are properly evaluated, retardance entered between orthogonal components of a beam of electromagnetic radiation which passes through each of said input and output lenses and interacts with said material system in a plane of incidence thereto can be independently calculated from said parameterized equations, given wavelength;

e. obtaining a spectroscopic set of ellipsometric data with said parameterizable material system present on the means for supporting a material system, utilizing a beam of electromagnetic radiation provided by said source of electromagnetic radiation, said beam of electromagnetic radiation being caused to pass through said input lens, interact with said parameterizable material system in a plane of incidence thereto, and exit through said output lens and enter said detector system;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input lens, interact with said material system in a plane of incidence thereto, and exit through said output lens.

The end result of practice of said method is that application of said parameterized equations for each of said input lens, output lens and material system for which values of parameters therein have been determined in step f., enables independent calculation of retardance entered between orthogonal components of a beam of electromagnetic radiation by each of said input and output lenses, and said material system, at given wavelengths in said spectroscopic set of ellipsometric data. And, it is emphasized that said calculated retardance values for each of said input lens, output lens and material system are essentially uncorrelated.

It is further to be appreciated that one of said input or output lenses can be physically absent entirely, which is the equivalent to considering it to be simply surrounding ambient atmosphere with associated non-birefringent properties. The language "providing spatially separated input and output lenses, at least one of said input and output lenses demonstrating birefringence when a beam of electromagnetic radiation is caused to pass therethrough", is to be interpreted to include such a situation wherein a non-birefringent lens is simply atmospheric ambient or an optical equivalent. Additionally, it is to be understood that input optical elements can comprise beam directing means and window(s), (as in a vacuum chamber), in addition to input lens(es); and that optput optical elements can comprise selection beam directing means and window(s), (as in a vacuum chamber), as well as output lens(es).

As further discussed later herein, a modification to the just recited method can be to, (in the step d. provision of a mathematical model for said ellipsometer system and said input and output lenses and said parameterizable material system for each of said input and output lenses), provide separate parameterized mathematical model parameterized equations for retardance entered to each of said two orthogonal components of a beam of electromagnetic radiation caused to pass through said input and output lenses. When this is done, at least one of said orthogonal components for each of said input and output lenses is directed out of the plane of incidence of said electromagnetic beam onto said parameterizable material system. And, typically, though not necessarily, one orthogonal component will be aligned with the plane of incidence of said electromagnetic beam onto said parameterizable material system. When this is done, calculation of retardation entered between orthogonal components of said beam of electromagnetic radiation, given wavelength, by said input lens is provided by comparison of retardance entered to each of said orthogonal components for said input lens, and such that calculation of retardation entered between orthogonal components of said beam of electromagnetic radiation, given wavelength, by said output lens is provided by comparison of retardance entered to each of said orthogonal components for said output lens.

It is pointed out that the step f. simultaneous evaluation of parameters in said mathematical model parameterized equations for said parameterizable material system, and for said input and output lenses, is typically, though not necessarily, achieved by a square error reducing mathematical curve fitting procedure.

It is important to understand that in the method recited earlier, the step b. positioning of an ellipsometer system source of electromagnetic radiation and an ellipsometer system detector system includes positioning a polarizer between said source of electromagnetic radiation and said input lens, and the positioning of an analyzer between said output lens and said detector system, and in which the step e. obtaining of a spectroscopic set of ellipsometric data typically involves obtaining data at a plurality of settings of at least one component selected from the group consisting of: (said analyzer and said polarizer). As well, it is to be understood that additional elements can also be placed between said source of electromagnetic radiation and said input lens, and/or between said output lens and said detector system, and that the step e. obtaining of a spectroscopic set of ellipsometric data can involve, alternatively or in addition to the recited procedure, obtaining data at a plurality of settings of at least one of said additional components.

It is also to be understood that the step of providing separate parameterized mathematical model parameterized equations for enabling independent calculation of retardance entered by said input said output lenses between orthogonal components of a beam of electromagnetic radiation caused to pass through said input and output lenses preferably involves parameterized equations having a form selected from the group consisting of:

$$ret(\lambda)=(K1/\lambda)$$

$$ret(\lambda)=(K1/\lambda)*(1+(K2/\lambda 2))$$

$$ret(\lambda)=(K1/\lambda)*(1+(K2/\lambda 2)+(K3/\lambda 4))$$

A modified method of accurately evaluating parameters in parameterized equations in a mathematical model of a system of spatially separated input and output lenses, said parameterized equations enabling, when parameters therein are properly evaluated, independent calculation of retardation entered by each of said input lens and said output lens to at least one orthogonal component(s) of a beam of electromagnetic radiation caused to pass through said input and output lenses, at least one of said input and output lenses being birefringent, said method comprising, in a functional order, the steps of:

a. providing spatially separated input and output lenses, at least one of said input and output lenses demonstrating birefringence when a beam of electromagnetic radiation is caused to pass therethrough, there being a means for supporting a material system positioned between said input and output lenses;

b. positioning an ellipsometer system source of electromagnetic radiation and an ellipsometer system detector system such that in use a beam of electromagnetic radiation provided by said source of electromagnetic radiation is caused to pass through said input lens, interact with said material system in a plane of incidence thereto, and exit through said output lens and enter said detector system;

c. providing a material system to said means for supporting a material system;

d. providing a mathematical model for said ellipsometer system and said input and output lenses and said material system, comprising, for each of said input lens and said output lens, separate parameterized equations for retardance for at least one orthogonal component in a beam of electromagnetic radiation provided by said source of electromagnetic radiation, which orthogonal component is directed out of a plane of incidence which said electromagnetic beam makes with said material system in use, and optionally providing separate parameterized equations for retardance for an in-plane orthogonal component of said beam of electromagnetic radiation, such that retardation entered to said out-of-plane orthogonal component, and optionally to said in-plane orthogonal component, of said beam of electromagnetic radiation by each of said input and output lenses, can, for each of said input and output lenses, be separately calculated by said parameterized equations, given wavelength, where parameters in said parameterized equations are properly evaluated;

e. obtaining a spectroscopic set of ellipsometric data with said material system present on the means for supporting a material system, utilizing a beam of electromagnetic radiation provided by said source of electromagnetic radiation, said beam of electromagnetic radiation being caused to pass through said input lens, interact with said material system in a plane of incidence thereto, and exit through said output lens and enter said detector system;

f. by utilizing said mathematical model provided in step d. and said spectroscopic set of ellipsometric data obtained in step e., simultaneously evaluating material system DELTA'S in correlation with in-plane orthogonal component retardance entered to said beam of electromagnetic radiation by each of said input and output lenses, and parameters in said mathematical model parameterized equations for out-of-plane retardance entered by said input lens and said output lens to a beam of electromagnetic radiation caused to pass through said input lens, interact with said material system in said plane of incidence thereto, and exit through said output lens.

Again, application of said parameterized equations for out-of-plane retardance entered by said input lens and said output lens to a beam of electromagnetic radiation caused to pass through said input lens, interact with said material system in said plane of incidence thereto, and exit through said output lens, for which values of parameters therein are determined in step f., enables independent calculation of retardance entered to said out-of-plane orthogonal component of a beam of electromagnetic radiation by each of said input and output lenses, given wavelength.

Also, again the step f. simultaneous evaluation of parameters in said mathematical model parameterized equations for calculation of retardance entered to said out-of-plane orthogonal component of a beam of electromagnetic radiation by each of said input and output lenses, given wavelength, and said correlated material system DELTA'S and retardance entered to said in-plane orthogonal component of a beam of electromagnetic radiation by each of said input and output lenses, is typically achieved by a square error reducing mathematical curve fitting procedure.

It remains, in said method, to definitely provide values for parameters in the in-plane parameterized equations for retardation, in said mathematical model of a system of spatially separated input and output lenses. Said method therefore further comprises the steps of:

g. providing a parameterized equation for retardation entered by said material system to the in-plane orthogonal component of a beam of electromagnetic radiation, and as necessary similar parameterized equations for retardation entered by each of said input and output lenses to the in-plane orthogonal component of a beam of electromagnetic radiation; and h. by utilizing said parameterized mathematical model provided in step d. and said spectroscopic set of ellipsometric data obtained in step e., simultaneously evaluating parameters in said mathematical model parameterized equations for independent calculation of retardance entered in-plane by said material system and by said input lens and said output lens such that the correlation between material system DELTA'S and the retardance entered by said in-plane orthogonal component of a beam of electromagnetic radiation by each of said input and output lenses, at given wavelengths in said spectroscopic set of ellipsometric data, is broken.

The end result of practice of the immediately foregoing steps a.–h. is that application of said parameterized equations for each of said input lens, output lens and material system for which values of parameters therein have been determined in step h., enables independent calculation of retardance entered to both said out-of-plane and said in-plane orthogonal components of a beam of electromagnetic radiation by each of said input and output lenses, and retardance entered by said material system to said in-plane orthogonal component of said beam of electromagnetic radiation, at given wavelengths in said spectroscopic set of ellipsometric data.

As before for other parameter evaluation steps, the step h. simultaneous evaluation of parameters in said mathematical model parameterized equations for said in-plane retardation entered by said parameterized material system, and said input and output lenses, is typically achieved by a square error reducing mathematical curve fitting procedure.

If the material system present can not be easily parameterized, said method of accurately evaluating parameters in parameterized equations in a mathematical model of a system of spatially separated input and output lenses, provides that the following steps, g.–j. be practiced:

g. removing the material system from said means for supporting a material system positioned between said input and output lenses, and positioning in its place an alternative material system for which a parameterized equation for calculating in-plane retardance entered to a beam of electromagnetic radiation, given wavelength, can be provided;

h. providing a parameterized equation for retardation entered in-plane to an orthogonal component of a beam of electromagnetic radiation by said alternative material system which is then positioned on said means for supporting a material system positioned between said input and output lenses, and as necessary similar parameterized equations for retardation entered by each of said input and output lenses to the in-plane orthogonal component of a beam of electromagnetic radiation;

i. obtaining a spectroscopic set of ellipsometric data with said alternative material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system;

j. by utilizing said parameterized mathematical model for said input lens and said output lens provided in step d. and said parameterized equation for retardance entered by said alternative material system provided in step h., and said spectroscopic set of ellipsometric data obtained in step i., simultaneously evaluating parameters in said mathematical model parameterized equations for independent calculation of retardance entered to an in-plane orthogonal component of said beam of electromagnetic radiation by said alternative material system and by said input lens and said output lens, such that correlation between DELTA'S entered by said alternative material system and retardance entered by said in-plane orthogonal component of said beam of electromagnetic radiation, by each of said input and output lenses, at given wavelengths in said spectroscopic set of ellipsometric data, is broken, said simultaneous evaluation optionally providing new values for parameters in parameterized equations for calculation of retardance entered in said out-of-plane components of said beam of electromagnetic radiation by each of said input lens and said output lens;

The end result being that application of said parameterized equations for each of said input lens and output lens and alternative material system, for each of which values of parameters therein have been determined in step j., enables independent calculation of retardance entered to both said out-of-plane and said in-plane orthogonal components of a beam of electromagnetic radiation by each of said input lens and said output lens, and retardance entered by said alternative material system to said in-plane orthogonal component of a beam of electromagnetic radiation, at given wavelengths in said spectroscopic set of ellipsometric data.

As before, said method of accurately evaluating parameters in parameterized equations in a mathematical model of a system of spatially separated input and output lenses provides that in the step j. simultaneous evaluation of parameters in said mathematical model parameterized equations for said in-plane retardation entered by said parameterized material system, and at least said in-plane input lens and output lens, is typically achieved by a square error reducing mathematical curve fitting procedure.

As mentioned with respect to the first method disclosed above, said method of accurately evaluating parameters in parameterized equations in a mathematical model of a system of spatially separated input and output lenses also provides that the step b. positioning of an ellipsometer system source of electromagnetic radiation and an ellipsometer system detector system includes positioning a polarizer between said source of electromagnetic radiation and said input lens, and the positioning of an analyzer between said output lens and said detector system, and in which the step e. obtaining of a spectroscopic set of ellipsometric data involves obtaining data at a plurality of settings of at least one component selected from the group consisting of: (said analyzer and said polarizer). As well, it is again to be understood that additional elements can also be placed between said source of electromagnetic radiation and said input lens, and/or between said output lens and said detector system, and that the step e. obtaining of a spectroscopic set of ellipsometric data can involve, alternatively or in addition to the recited procedure, obtaining data at a plurality of settings of at least one of said additional components.

Said method of accurately evaluating parameters in parameterized equations in a mathematical model of a system of spatially separated input and output lenses also provides that the step of providing separate parameterized mathematical model parameterized equations for enabling independent calculation of out-of-plane and in-plane retardance entered by said input said output lenses to said beam of electromagnetic radiation caused to pass through said input and output lenses involve parameterized equations having a form selected from the group consisting of:

$$ret(\lambda)=(K1/\lambda)$$

$$ret(\lambda)=(K1/\lambda)*(1+(K2/\lambda2))$$

$$ret(\lambda)=(K1/\lambda)*(1+(K2/\lambda2)+(K3/\lambda4))$$

It is again noted that while said method can be practiced with any type "lenses", be there one or two of them, (ie. one, or both, of the input or output lenses can be essentially non-birefringent and even ambient), and while an input lens or output lens can be considered to be formed by a plurality of elements, (eg. two elements made of different materials such as Fused Silica and Calcium Fluoride), the step a. providing of spatially separated input and output lenses is best exemplified as being practiced by the providing of an ellipsometer system that has both input and output lenses present therein through which an beam of electromagnetic radiation is caused to convergently enter and exit in a recolliminated form, repectively.

Any of the described methods can further involve, in a functional order, the following steps a1.–a4:

a1. fixing evaluated parameter values in mathematical model parameterized equations, for each of said input lens and output lens, such that said parameterized equations allow independent determination of retardation entered between orthogonal components of a beam of electromagnetic radiation caused to pass through said input and output lenses, given wavelength; and a2. causing an unknown material system to be present on said means for supporting a material system;

a3. obtaining a spectroscopic set of ellipsometric data with said unknown material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system; and a4. by utilizing said mathematical model for said input lens and said output lens in which parameter values in mathematical model parameterized equations, for each of said input lens and output lens have been fixed, simultaneously evaluating PSI'S and uncorrelated DELTA'S parameters for said unknown material system.

As in other steps in said method in which parameter values are evaluated, it is again noted that the method of accurately evaluating parameters in parameterized equations in a mathematical model of a system of spatially separated input and output lenses in which said simultaneous evaluation of PSI'S and DELTA'S for said unknown material are typically achieved by a square error reducing mathematical curve fitting procedure.

As alluded to earlier, the step of providing spatially separated input and output lenses, at least one of said input and output lenses demonstrating birefringence when a beam of electromagnetic radiation is caused to pass therethrough, can involve one or both lens(es) which is/are not birefringent. And, said at least one lens which is not birefringent can be essentially a surrounding ambient, (ie. a phantom lens which is essentially just the atmosphere surrounding a material system).

It is noted that where parameters in parameterized equations for out-of-plane retardance equations have been determined, a focused version of the method for accurately evaluating parameters in parameterized equations in a mathematical model of a system of spatially separated input and output lenses can comprise the steps of b1–b7:

b1. fixing evaluated parameter values in mathematical model parameterized equations, for each of said input lens and output lens, such that said parameterized equations allow independent determination of retardation entered between orthogonal components of a beam of electromagnetic radiation caused to pass through said input and output lenses, given wavelength; and b2. causing an unknown material system to be present on said means for supporting a material system;

b3. obtaining a spectroscopic set of ellipsometric data with said unknown material system present on the means for supporting a material system, utilizing a beam of electromagnetic radiation provided by said source of electromagnetic radiation, said beam of electromagnetic radiation being caused to pass through said input lens, interact with said alternative material system in a plane of incidence thereto, and exit through said output lens and enter said detector system; and b4. by utilizing said mathematical model for said input lens and said output lens in which parameter values in mathematical model parameterized equations, for each of said input lens and output lens have been fixed, simultaneously evaluating ALPHA'S and BETA'S for said unknown material system, (see the Detailed Description for definition of ALPHA'S and BETA'S);

b5. applying transfer functions to said simultaneously evaluated ALPHA'S and BETA'S for said unknown material system to the end that a data set of effective PSI's and DELTA's for a combination of said lenses and said material system is provided;

b6. providing a mathematical model for said combination of said lenses and said material system which separately accounts for the retardation effects of the presence of said lenses and said material system by parameterized equations; and b7. by utilizing said mathematical model for said combination of said lenses and said material system which separately accounts for the effects of the presence of at least said lenses by parameterized equations; and said data set of effective PSI's and DELTA's for a combination of said lenses and said material system, simultaneously evaluating actual PSI's and DELTA's for said unknown material system per se.

In the case, for instance, where the ellipsometer involved is a Rotating Analyzer, or Rotating Polarizer ellipsometer system, (but not where the ellipsometer involved is a Rotating Compensator System), it is noted that determination of "Handedness" is required. Therefore the foregoing method can include, as necessary, providing a mathematical model for said combination of said lenses and said material system which separately accounts for the retardation effects of the presence of said lenses and said material system by parameterized equations which further includes providing for the effects of Handedness. It is specifically stated that where the approach of regressing onto effective PSI and DELTA values, (as determined in step b7.), is utilized, the mathematical model can be derived so that "Handedness" is accounted for in arriving at actual PSI's and DELTA's for said unknown material system per se.

As a general comment it is to be understood that separate PSI and DELTA values are achieved for each angle of incidence a beam of electromagnetic radiation makes with respect to a material substrate and for each wavelength utilized in a spectroscopic range of wavelengths.

Also, as said methodology finds application in ellipsometer systems in which are present input and/or output lenses, the foregoing methods of use are recited utilizing specific reference to input and output lenses in ellipsometer systems. In general said methodology can be applied where any input and/or output optical elements are present.

While the forgoing has presented method steps in a logical sequence to enhance disclosure, it is to be understood that the steps of any method recitation in this Specification can be practiced in any functional order.

Patents which specifically focus on the use of lenses, preferrably achromatic, in ellipsometry and related systems are:

U.S. Pat. Nos. 5,877,859 and 5,798,837 to Aspnes et al.;
U.S. Pat. No. 5,333,052 to Finarov;
U.S. Pat. No. 5,608,526 to Piwonka-Corle et al.;
U.S. Pat. No. 5,793,480 to Lacy et al.;
U.S. Pat. Nos. 4,636,075 and 4,893,932 to Knollenberg; and
U.S. Pat. No. 4,668,860 to Anthon.
U.S. Pat. No. 5,917,594 to Norton.
U.S. Pat. No. 5,166,752 to Spanier et al.

U.S. Pat. No. 6,493,097 to Ivarsson is disclosed as it describes an imaging ellipsometer which comprises a two dimensional array detector.

U.S. Pat. No. 5,596,406 to Rosencwaig et al., is disclosed as it describes an ellipsometer which comprises a two dimensional array.

Published Patent Application No. US2002/0163634 by Meeks et al. is disclosed as it describes controling spot size in profilometer, ellipsometer, reflectometer and scatterometer.

Patent to Johs et al., U.S. Pat. No. 5,936,734, describes the use a beam of electromagnetic radiation to investigate a sample which has a plurality of regions which have thin films of different relative thicknesses, and/or are comprised of different materials, is complicated by the fact that components of said beam reflected by different regions of the sample can add in two different modes, namely coherent and incoherent. Said 734 Patent taught that a partition parameter, which accounted for the percentage of a reflected beam that adds coherently and incoherently, should be a part of the mathematical model of the sample and system used to do the analysis. Many other references exist which describe similar difficulties which arise when using electromagnetic radiation to investigate non-homogeneous samples.

PCT Application WO 01/086257 describes use of an aperture and lens to define spot size of a beam of electromagentic radiation on a sample.

A paper by Johs, titled "Regression Calibration Method for Rotating Element Ellipsometers", Thin Solid Films, 234 (1993) is also disclosed as it describes a mathematical regression based approach to calibrating ellipsometer systems, including characterizing a sample.

Finally, while the approach of the 734 Patent provides benefit, it can be difficult to arrive at unambiguous results where a beam partitioning factor is involved. Need remains for a more definite approach to investigating samples which have a plurality of regions which have thin films of different relative thicknesses, and/or are comprised of different materials.

DISCLOSURE OF THE INVENTION

The presently disclosed invention teaches that the primary approach to providing analysis of small spots on samples, such as non-homogeneous samples, should be to probe or analyze specific regions thereof independently, although said approach can be supplemented by accounting for partitioning between incoherent and coherent addition of beam components which reflect from non-homogeneous samples, (ie. surface topology depth varies from point to point and/or different regions of the sample surface are comprised of different materials).

The present invention can involve sequentially applying constant dimension beam spot (where the beam impinges upon the sample), size over a range of wavelengths, to the same or different locations on a sample, and/or can involve imaging reflected electromagnetic radiation with a two dimensional array, and selectively analyzing portions of the beam which are detected by selected detector elements therewithin.

System

The present invention system, in a preferred embodiment, provides capability to adjust the size of a spot of electromagnetic radiation caused to impinge on a sample by focusing or defocused the beam applied to a sample. The purpose is to enable provision of a spot size which is appropriate to detect desired features of a sample. For example, using a theoretical point size beam spot to investigate a grating will provide very different results than will be obtained if the beam spot size is sufficient to include a multiplicity of grating peaks and troughs. The point size beam spot will investigate only a small portion of one peak or trough while the larger beam size spot will provide a result corresponding to an average of the characteristics over many peaks and troughs.

In its most basic sense, the present invention comprises a system which sequentially comprises a source of electromagnetic radiation, variable means for effecting focus or defocus of a beam of electromagnetic radiation provided by said source of electromagnetic radiation, a stage for supporting a sample, and a detector. In use an electromagnetic beam is provided by said source of electromagnetic radiation and is caused to pass through said means for effecting focus or defocus thereof which applies focus or defocus thereto such that a desired spot size is achieved on said sample, then reflects from said sample and enters said detector. The source of electromagnetic radiation is preferably spectroscopic and said means for effecting focus or defocus thereof is preferably programmable to functionally correlate a specific degree of focus or defocus with each wavelength. Said system can further comprise a monochromator to select specific wavelengths and in which said means for effecting focus or defocus is programmable to functionally correlate a specific degree of focus or defocus with each monochromator selected wavelength. Additionally, or alternatively, the detector can comprise a multiplicity of detector elements and a dispersive element be positioned to receive electromagnetic radiation reflected from a sample and provide different wavelengths to different detector element. Said detector and means for effecting focus or defocus is again, functionally correlated such that data is accepted from a detector element only when a specific degree of focus or defocus is appropriate for the wavelength received thereby.

The present invention can also be described as a system for investigating a sample sequentially comprising a spectroscopic source of electromagnetic radiation, a monochromator, variable means for effecting focus or defocus of a beam of electromagnetic radiation provided by said source of electromagnetic radiation, a stage for supporting a sample, and a detector. In use a spectroscopic beam of electromagnetic radiation is provided by said source of electromagnetic radiation, said monochrometor selects a specific wavelength, and said means for effecting focus or defocus thereof applies focus or defocus thereto as a function of monochromator selected wavelength, such that a desired spot size is achieved on said sample, then reflects from said sample and enters said detector.

A modified embodiment of the present invention can be described as a system for investigating a sample comprising a spectroscopic source of electromagnetic radiation, a stage for supporting a sample and a detector, there being a sample positioned on said stage for supporting a sample, said system further comprising a two-dimensional detector array which comprises a multiplicity of detector elements, said two-dimensional detector array being positioned such that different detector elements receive electromagnetic radiation reflected from different locations on said sample. In use a spectroscopic beam of electromagnetic radiation is provided by said source of electromagnetic radiation and said spectroscopic beam then being reflected from said sample and enter said two dimensional detector. The method of use of said system is characterized in that data from specific groups of detector elements are analyzed separately from data detected by other detector elements. Said system can further comprise a variable means for effecting focus or defocus of a beam of electromagnetic radiation onto said sample, and a monochromator, wherein said means for effecting focus or defocus of a beam of electromagnetic radiation onto said sample and said monochromator are functionally correlated such that at any selected wavelength the spot size of said electromagnetic beam on said sample is maintained constant.

While not limiting to the present invention, a lens system which is particularly well suited for application in ellipsometer and the like systems provides for spectroscopic electromagnetic beam spot size and focal length chromatic dispersion reduction by configuring at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation. Such a lens system can be characterized by a converging element which presents as a selection from the group consisting of:

a bi-convex;

a plano-convex with an essentially flat side;

and a diverging element which is characterized as a selection from the group consisting of:

a bi-concave lens element;

a plano-concave with an essentially flat side.

Further a lens system with application in the present invention can comprise a selection from the group consisting of:

a) a sequential combination of a bi-convex element and a bi-concave element;

b) a sequential combination of a bi-concave element and a bi-convex element;

c) a sequential combination of a bi-convex element and a plano-concave element with said concave side of said plano-concave element adjacent to said bi-convex element;

d) a sequential combination of a bi-convex element and a plano-concave element with said essentially flat side of said plano-concave element being adjacent to said bi-convex element;

e) a sequential combination of a plano-concave element and a bi-convex element with said essentially flat side of said plano-concave element adjacent to said bi-concave element;

f) a sequential combination of a plano-concave element and bi-convex element with said concave side of said plano-concave element adjacent to said bi-convex element;

g) a sequential combination of a plano-convex element and a bi-concave element with said essentially flat side of said plano-convex element adjacent to said bi-concave element;

h) a sequential combination of a bi-concave element with a plano-convex element with said convex side of said plano-convex element adjacent to said bi-concave element;

i) a sequential combination of a plano-concave element and a plano-convex element with the essentially flat side of said plano-concave element being adjacent to the convex side of the plano-convex element;

j) a sequential combination of a plano-concave element and a plano-convex element with the essentially flat side of said planoconcave element being adjacent to the convex side of said plano-convex element;

k) a sequential combination of a plano-convex element and a plano-concave element with the essentially flat side of said plano-convex element and the essentially flat side of said plano-concave element being adjacent to one another;

l) a sequential combination of a plano-concave element and a plano-convex element with the concave side of said plano-concave element being adjacent to the convex side of the plano-convex element;

m) a sequential combination of a plano-convex element and a bi-concave element with said convex side of said plano-convex element adjacent to said bi-concave element;

n) a sequential combination of a bi-concave element and a plano-convex element with said essentially flat side of said plano-convex element adjacent to said bi-concave element;

o) a sequential combination of a plano-convex element and a plano-concave element with said convex side of said plano-convex element adjacent to the concave side of the plano-concave element;

p) a sequential combination of a plano-concave element and a plano-convex element with said essentially flat side of said plano-convex element being adjacent to the essentially flat side of the plano-concave element;

q) a sequential combination of a plano-convex element and a plano-concave element with said convex side of said plano-convex element being adjacent to the essentially flat side of the plano-concave element; and r) a sequential combination of a plano-concave element with a plano-convex element with the essentially flat side of said plano-convex element being adjacent to the concave side of said plano-concave element;

s) t) a sequential combination of three elements.

and wherein said region between said first and second elements having essentially the optical properties of a selection from the group consisting of:

a void region; and a functional equivalent to a void region;

and a transparent bonding agent.

(It is noted that the listing of single two element lens constructions (a) through (r) above provides insight to applicable converging and diverging lens element combinations in dual stage lens systems).

A lens system with application in a present invention system can be further characterized in that the converging element of said first and second elements is typically made of a material independently selected from the group consisting of:

CaF;

BaF$_2$;

LiF; and

MgF$_2$;

and the diverging element of said first and second elements is selected to be made of fused silica, although it is within the scope of the present invention to make the converging element of fused silica and the diverging element of a selection from the group consisting of CaF$_2$; BaF$_2$; LiF; and MgF$_2$. It is noted that lens elements made of MgF$_2$ are typically bi-refringent whereas lens elements made of CaF$_2$; BaF$_2$ and LiF typically demonstrate far less bi-refringence, unless subjected to stress.

A lens system with a focal length of fifty millimeters or less, with application in present invention systems, can be described as being comprised of lens system comprising two sequentially oriented lenses, each of said sequentially oriented lenses being comprised of:

at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation; said lens system being described by a selection, from the group consisting of:

1. a sequential combination of a converging element (C), a diverging element (D), a converging element (C) and a diverging element (D);
2. a sequential combination of a converging element (C), a diverging (D) element, a diverging (D), element and a converging (C) element;
3. a sequential combination of a diverging element (D), a converging element (C), a diverging (D) element and a converging (C) element;
4. a sequential combination of a diverging element (D), a converging element (C), a converging element (C) and a diverging (D) element.

And, of course, other sequential lens element configurations within the scope of application in the present invention include:

(Converging(C)) (Converging(C)) (Diverging(D));

(Diverging(D)) (Diverging(D)) (Converging(C));

(Converging(C)) (Diverging(D)) (Diverging(D));

(Diverging(D)) (Converging(C)) (Diverging(D));

(Converging(C)) (Converging(C)) (Diverging(D)) (Diverging(D)); and (Diverging(D)) (Diverging(D)) (Converging(C)) (Converging(C)).

One embodiment of a lens system suitable for application in the present invention is further characterized by at least one selection from the group consisting of:

a. the focal length of the lens system is between forty (40) and forty-one (41) millimeters over a range of wavelengths of at least two-hundred (200) to seven-hundred (700) nanometers; and b. the focal length of the dual stage lens system varies by less than five (5%) percent over a range of wavelengths of between two-hundred and five-hundred nanometers; and c. the spot diameter at the focal length of the lens system is less than seventy-five (75) microns over a range of wavelengths of at least two-hundred (200) to seven-hundred (700) nanometers.

It is specifically noted that the present invention includes the case of an ellipsometer or the like system in which only one of said multi-element input or output lenses is present, (typically only the input lens), and the case wherein both input and output lenses are present, but only one is of multiple element construction, and/or demonstrates bi-refringence.

A preferred present invention single two element lens system is constructed from a Bi-convex lens element made of CaF$_2$, (eg. JANOS Technology Inc. Part No. A1407-003), functionally combined with a Fused Silica Plano-Concave lens element, (eg. OptoSigma Inc. Part No. 012-0080), in a manner generally indicated by FIG. 7e.

It is also disclosed that a lens system can comprise at least one cavity therein, said cavity having means for entering a flowable material such as a powder, fluid or liquid thereinto. Depending on the fluid entered to said at least one cavity, a system comprising an effective multi-element lens with refractive properties at various wavelengths which depend on the flowable material caused to be present in said cavity is effected. Further, the flowable material can be removed from the cavity and replaced by another, thereby providing a system with different refractive properties at various wavelengths. It should be appreciated that a filled cavity is an effective lens element in the disclosed invention system. In this light, it is to also be appreciated that a consideration in constructing previously known multiple element lenses involves physical interconnection between elements. Rigid elements must be shaped to sequentially fit one element to the next. It would be of benefit if a generic system could be provided which could be tailored to have desired achromatic effects on multiple wavelengths without modifying rigid components. A multiple cavity system can have different flowable materials present in at least two of the cavities, thereby allowing the achieving of desired refraction at various wavelengths. Substantially achromatic lenses can be achieved in this way, therefore it is disclosed that a present invention focusing element (lens) system can comprise at least one cavity filled with a flowable material, wherein said flowable material can be selected from the group consisting of:

powder;

fluid;

liquid;

water base liquid;

oil base liquid.

Further a cavity can be a selection from the group consisting of:

at least one concave side at an interface between an effective element and a cavity boundary;

at least one convex side at an interface between an effective element and a cavity boundary;

at least one flat side at an interface between an effective element and a cavity boundary;

two concave sides at an interfaces between an effective element and a cavity boundaries;

two convex sides at an interfaces between an effective element and a cavity boundaries;

two flat sides at an interfaces between an effective element and a cavity boundaries;

one concave side and one convex interface between an effective element and a cavity boundaries;

one concave side and one flat interface between an effective element and a cavity boundaries.

Methodology

Continuing, a present invention method of investigating a specifically defined area on a sample comprises the steps of:

a) providing a system for investigating a sample comprising a spectroscopic source of electromagnetic radiation, a stage for supporting a sample and a detector, said system further comprising a monochromator and variable means for effecting focus or defocus of a beam of electromagnetic radiation provided by said source of electromagnetic radiation, at the location where said beam impinges on a surface of a sample positioned upon said stage, the purpose being, at a sequential plurality of wavelengths, to enable controlling spot beam size thereat;

b) placing a sample comprising a non-uniform surface on said stage for supporting a sample and determining a desired beam spot size at the location at which said beam impinges on said sample;

c) causing a beam of electromagnetic radiation from said source of electromagnetic radiation which is of a wavelength selected by said monochromator, to impinge on said surface of said sample;

d) for each of a sequence of wavelengths adjusting said variable means for effecting focus or defocus of a beam of electromagnetic radiation to provide a beam spot size at the location whereat said electromagnetic beam impinges on said non-uniform sample surface;

with the effect being that a spot of constant size on the surface of said sample is investigated at a plurality of wavelengths.

Said method can involve a detector which is a two dimensional array comprising a multiplicity of detector elements.

Said method can involve analyzing data acquired from a subset of the multiplicity of detector elements.

Another present invention method of investigating desired features of a sample surface comprises the steps of:

a) providing a system for investigating a sample comprising a source of electromagnetic radiation, a stage for supporting a sample and a two dimensional multi-element detector, said system further comprising variable means for effecting focus or defocus of a beam of electromagnetic radiation provided by said source of electromagnetic radiation, at the location where said beam impinges on a surface of a sample positioned upon said stage, the purpose being to enable controlling spot beam size thereat;

b) placing a sample on said stage for supporting a sample;

c) causing a beam of electromagnetic radiation from said source of electromagnetic radiation to impinge on a surface of said sample;

d) adjusting said variable means for effecting focus or defocus of a beam of electromagnetic radiation to provide a beam spot size at the location whereat said electromagnetic beam impinges on said sample surface;

such that electromagnetic radiation from said spot on said surface of said sample is reflected into said two dimensional multi-element detector; and selecting a subset of said detector elements in said detector for which to secure data, and analyzing said secured data.

Another method of investigating a specifically defined area on a sample comprises the steps of:

a) providing a system for investigating a sample which sequentially comprises a spectroscopic source of electromagnetic radiation, a monochromator, variable means for effecting focus or defocus of a beam of electromagnetic radiation provided by said source of electromagnetic radiation, a stage for supporting a sample, and a detector, such that in use an electromagnetic beam is provided by said source of electromagnetic radiation and is caused to pass through said monochromator and means for effecting focus or defocus thereof, interact with said sample and enter said detector:

repeating steps b through d, a multiplicity of times:

b) causing said spectroscopic source to provide a beam of electromagnetism and direct it into said monochromater, which monochromator passes a desired wavelength in said spectroscopic beam and directs it into said variable means for effecting focus or defocus of a beam of electromagnetic radiation;

c) for each wavelength causing said variable means for effecting focus or defocus of a beam of electromagnetic radiation to provide a predetermined defocused spot size on said sample, such that said beam of electromagnetism interacts with said sample, and enters said detector; and d) for each wavelength causing said detector to acquire data which corresponds to a predetermined spot size which is the same size at each wavelength;

with the effect being that a spot on the surface of said sample is investigated at a plurality of wavelengths.

Another method of investigating a specifically defined area on a sample comprises the steps of:

a) providing a system for investigating a sample which sequentially comprises a spectroscopic source of electromagnetic radiation, variable means for effecting focus or defocus of a beam of electromagnetic radiation provided by said source of electromagnetic radiation, a stage for supporting a sample, and a detector;

such that in use an electromagnetic beam is provided by said source of electromagnetic radiation and is caused to pass through said means for effecting focus or defocus thereof, interact with said sample and enter said detector:

repeating steps b, c and d a multiplicity of times:

b) causing said spectroscopic source to provide a beam of electromagnetism and direct it into said variable means for effecting focus or defocus of a beam of electromagnetic radiation;

c) causing said variable means for effecting focus or defocus of a beam of electromagnetic radiation to provide a predetermined defocused spot size on said sample, such that said beam of electromagnetism interacts with said sample, and enters said detector; and d) for each row or column in a two dimensional array corresponding to the surface of said sample, causing said detector to acquire data corresponding at a multiplicity of column or row points respectively, and a multiplicity of wavelengths;

with the effect being that a three dimensional data set is developed corresponding to two dimensional surface data at each of a multiplicity of wavelengths.

In the preceding example methods, the variable means for effecting focus or defocus of a beam of electromagnetic radiation can be substantially achromatic and the variable means for providing a predetermined spot size on said sample set the same for each wavelength, or the variable means for effecting focus or defocus of a beam of electromagnetic radiation can be adjusted differently for at least two wavelengths. In either case an three dimensional data set is developed corresponding to two dimensional surface data at each of a multiplicity of wavelengths.

Said methods can include providing a system which further comprises a polarizer and analyzer ahead of and after said sample such that said system is an ellipsometer or polarimeter, and determining ellipsometric PSI and ellipsometric DELTA for said sample by a technique which compensates for birefringence of said variable means for effecting focus or defocus of a beam of electromagnetic radiation provided by said source of electromagnetic radiation, at the location where said beam impinges on a surface of a sample. Such methodology was disclosed in the Background Section and was previously taught in Pending application Ser. No. 09/583,229, and U.S. Pat. No. 6,034,777.

The present invention will be better understood by reference to the Detailed Description Section in combination with the Drawings.

BRIEF DESCRIPTION OF THE DRAWINGS

FIG. 1a and 1b show Spectrophotometer, and ellipsometer or polarimeter systems respectively.

FIGS. 4a and 4b show a diagram of a sample which comprises a plurality of regions which comprise different materials, and, respectively, a beam of electromagnetic radiation which is of a diameter sufficiently large to simultaneously encompass more than one said area, and a beam of electromagnetic radiation which is of a diameter sufficiently small to only impinge on an area made of only one material.

FIGS. 5a and 5b show a diagram of a sample which comprises a plurality of regions which comprise different topologies, and, respectively, a beam of electromagnetic radiation which is of a diameter sufficiently large to simultaneously encompass more than one said region, and a beam of electromagnetic radiation which is of a diameter sufficiently small to only impinge on a region made of only one material.

FIGS. 6a1–6a3 demonstate various approaches to controling spot size of a beam of electromagnetic radiation which impinges on a sample surface.

FIG. 7c shows a spot size of a beam of electromagnetic radiation which impinges on a sample surface for the achromatic, fused silica and CaF2 lenses of FIG. 7a.

FIGS. 8a–8g show lenses which comprise fluid filled cavities which can be applied as focusing means in the present invention.

DETAILED DESCRIPTION

FIG. 1a shows a Spectrophotometer System which comprises a Spectroscopic Source (LS) of a Beam of Electromagnetic Radiation, a Monochromator (M), a Sample (MS) atop a Stage (STG), and a Detector (DET). Importantly, there is also present a Spot Size Control (SSC) Means. The method of the present invention provides that during use the Monochromator (M) selects a Wavelength and the Spot Size Control (SSC) Means effects Focus or De-Focus such that at all Wavelengths the same Spot Size on the Surface of the Sample (MS) is achieved.

FIG. 1b shows an Ellipsometer or Polarimeter system, with both Reflection (RM) and Transmission (TM) beam pathways indicated. Although the transmission pathway is not shown in other Figures, where functionally relevant it is to be considered as incorporated thereinto. Shown are a Polarization State Generator comprised of a Source (LS) of a Beam of Electromagnetic Radiation, a Polarizer (P), and an optional Compensator (C) prior to a Sample (MS) atop a Stage (STG). After said Stage (STG), in the Reflection (RM) pathway is another optional Compensator (C'), an Analyzer (A) and Detector (DET). Beams (PPCLB) exiting said Polarizer (P) and (EPCLB) exiting said Analyzer (A) are also indicated. After said Stage (STG), in the Transmission (TM) pathway is another optional Compensator (C"), an Analyzer (A) and Detector (DET). Beams (PPCLB) exiting said Polarizer (P) and (EPCLB) exiting said Analyzer (A) are also indicated. As described with respect to the Spectrophotoemter, importantly as regards the present invention is the presence of Spot Size Control Means (SSC), and optionally (SSC') and (SSC"). Again, the Spot Size Control (SSC) Means serves to provide a constant Electromagnetic Beam Spot Size on a Surface of the Sample (MS) at the location whereat it impinges. In the method of the present invention said Spot Size Control (SSC) Means coordinates with a Wavelength control means, (eg. a Monochromator (M) placed after the Source (LS) for instance). It is beneficial at this point to refer to FIG. 7c which shows how various fixed focusing lenses provide variable Spot Sizes as a function of Wavelength. While an Achromatic Lens, (exemplary construction of which is demonstrated in FIG. 7d), provides relatively constant Spot Size, as compared to other lenses, even it provides a Spot Size on the surface of a Sample (MS), which varies with Wavelength. It is a purpose of the Method of the present invention to eliminate even such minimal Spot Size Variation vs. Wavelength, by effecting, as necessary, change of the Spot Size Control (SSC) means at each Wavelength. With such control applied it can be assured that the same area on a Sample (MS) Surface is being investigated at each Wavelength. It is to be understood that the Spot Size Control (SSC) can be a Means for effecting Focus and De-Focus of a Beam of Electromagnetic Radiation, as necessary.

Figure 2:
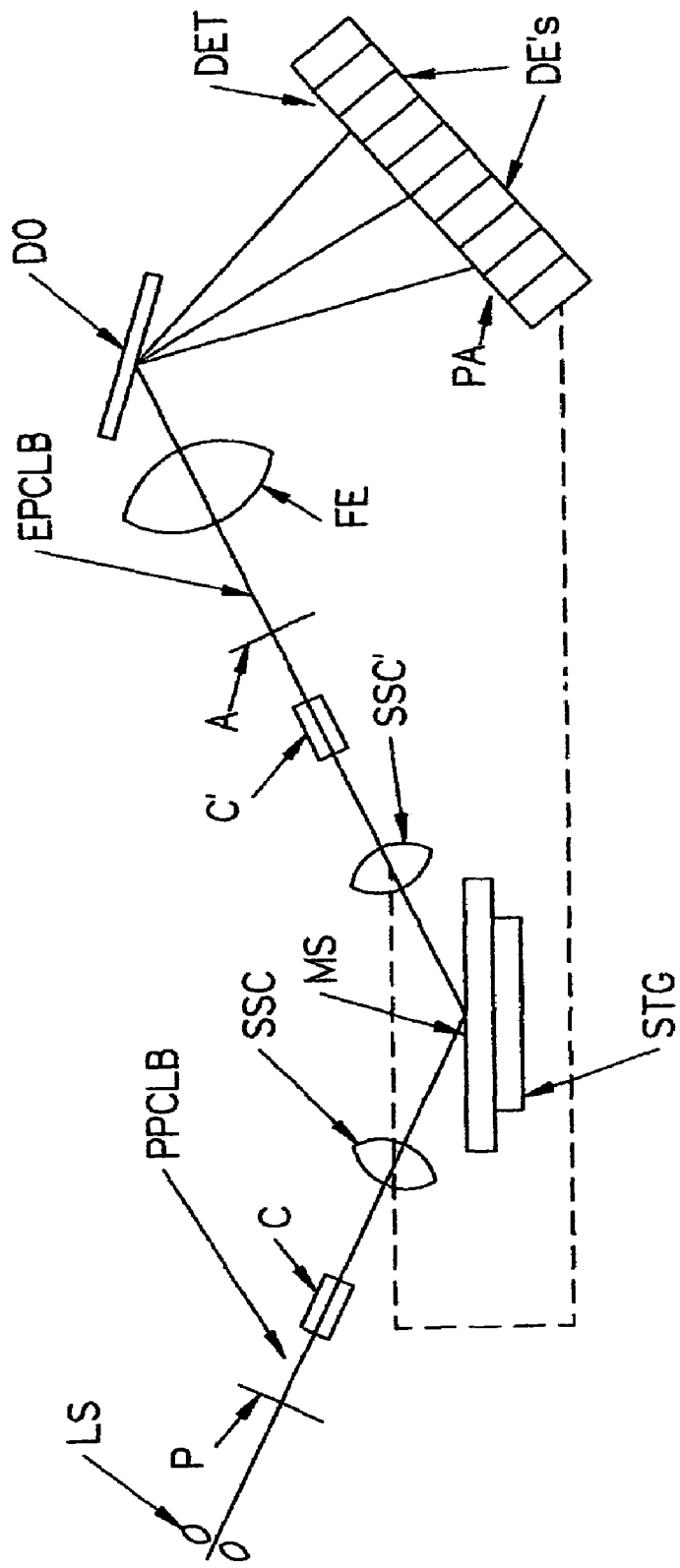
FIG. 2 shows an ellipsometer or polarimeter system which specifically includes dispersive optics and a multi-element detector.

FIG. 2 shows a Reflection Mode Ellipsometer or Polarimeter system which specifically includes Dispersive Optics and a Multi-Element Detector. Said embodiment comprises much the same elements as described with respect to the FIG. 1 embodiment, except that a Monochramater (M) is not included. Instead, a multiplicity of Wavelengths are simultaneously directed to interact with a Sample (MS), and they are directed via a Dispersive Optics (DO) into a Multi-Element (DE) Detector (DET), (which can be linear or two or more dimensional). In use, signal from specific Detector Elements (DE's) can be monitored in conjunction with a sequence of settings of the Spot Size Control (SSC) Means so that the same area on the Sample (MS) Surface is investigated at each Wavelength.

(Note that the dashed lines in FIGS. 1a, 1b and 2 represent control lines which carry signals between a Monochromator (M) the Spot Size Control (SSC) (SSC') (SSC") means, or between the Spot Size Control (SSC) (SSC') means and the Detector Elements (DE) containing Multi-dimensional Detector (DET)).

Figure 3:
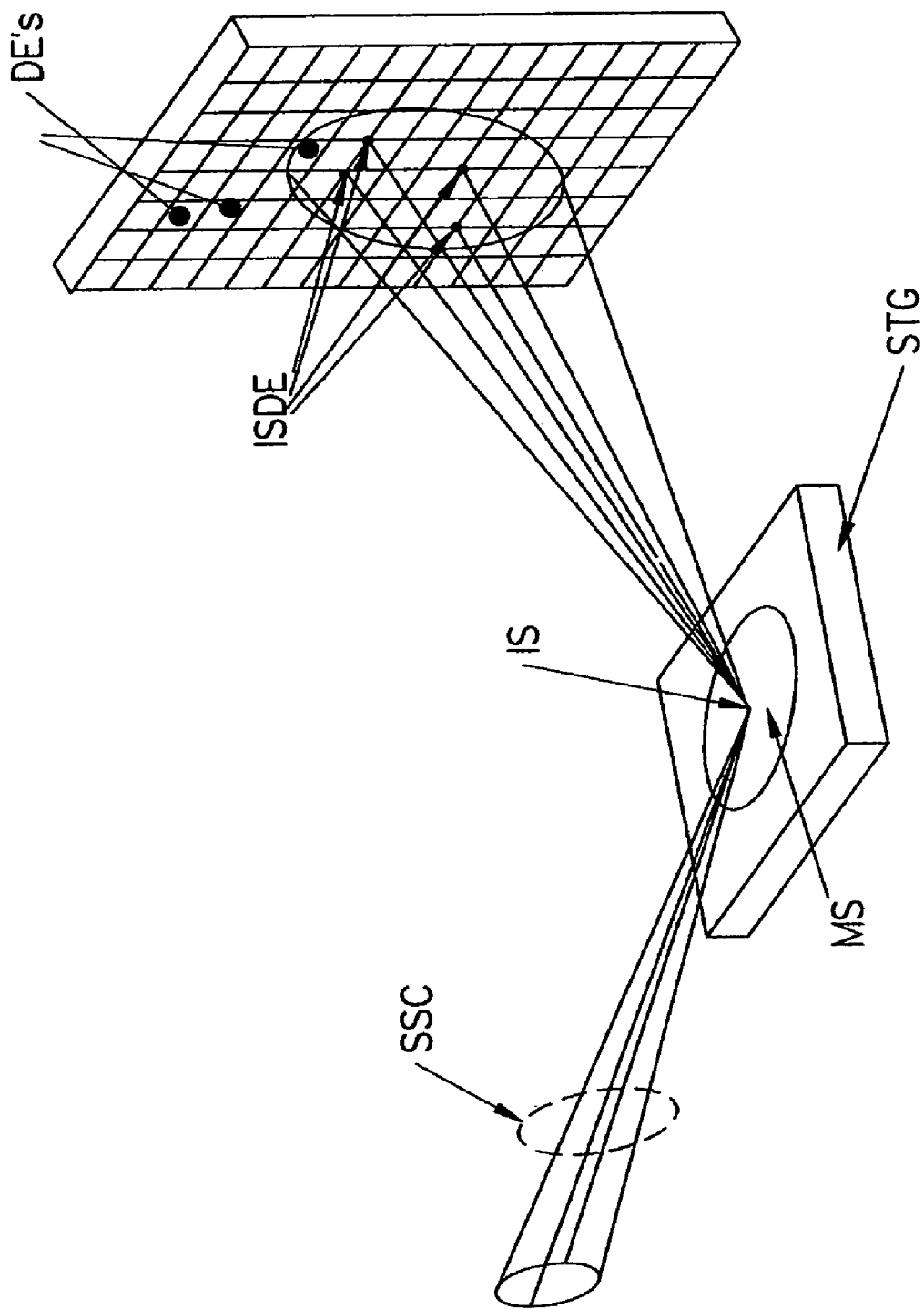
FIG. 3 shows that a multi-element detector can be two-dimensional.

FIG. 3 shows that a multi-element detector can be multi-dimensional, (eg. two-dimensional). Where this is the case the teachings associated with FIGS. 1a, 1b and 2 apply, but with a new focus. Said new focus being that selection of specific Detector Elements (DE) can be made from within said array of Detector Elements (DE), which selections correspond to specific areas of the Sample (MS) Surface. This can be practiced with coordinated change of the Spot Size Control (SSC) means with respect to Wavelength, but as only a small portion of the Spot is being monitored said effect is less critical than is the case in the FIGS. 1a, 1b and 2 scenarios. When operated as a Spectrophotometer, control of Spot Size can help prevent Intensity changes with Wavelength, which are artifacts of Spot Size change. Where Ellipsometry is practiced, as it is a ratio of "P" to "S" components of an electromagnetic beam that is monitored, this effect not so critical.

FIGS. 4a and 4b show diagrams of a sample which comprises a plurality of regions which comprise different materials, and, respectively, a beam of electromagnetic radiation which is of a diameter sufficiently large to simultaneously encompass more than one said area, and a beam of electromagnetic radiation which is of a diameter sufficiently small to only impinge on an area made of only one material as is an approach achievable under the teachings of the present invention method.

FIGS. 5a and 5b show a diagram of a sample which comprises a plurality of regions which comprise different topologies, and, respectively, a beam of electromagnetic radiation which is of a diameter sufficiently large to simultaneously encompass more than one said region, and a beam of electromagnetic radiation which is of a diameter sufficiently small to only impinge on a region made of only one material as is an approach achievable under the teachings of the present invention method.

Note that FIGS. 4b and 5b have well defined Input (BI) and Output (BO) Beams, whereas FIGS. 4a and 5a have very complex Output Beams, (eg. A1, B1, A2, B2, B2' in FIG. 4a and A, AB and B combinations in FIG. 5a).

Figure 6B:
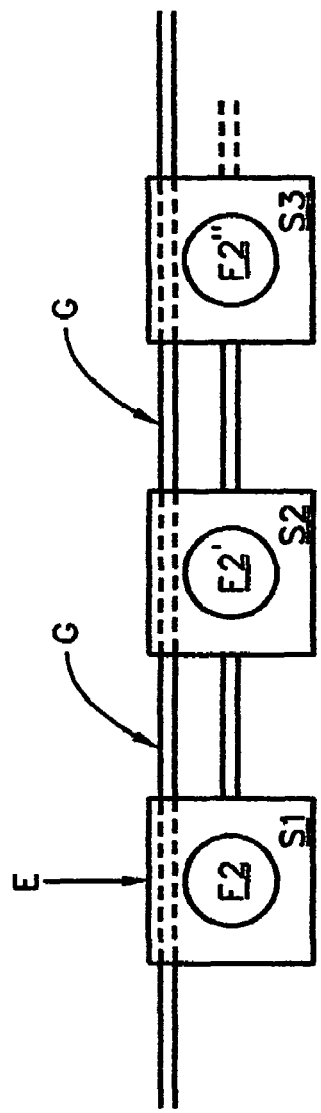
FIGS. 6b and 6c demonstrate an array of slidably mounted focusing elements which provide different focal lengths, and which can be sequentially positioned in the path of a beam of electromagnetic radiation.
Figure 6C:
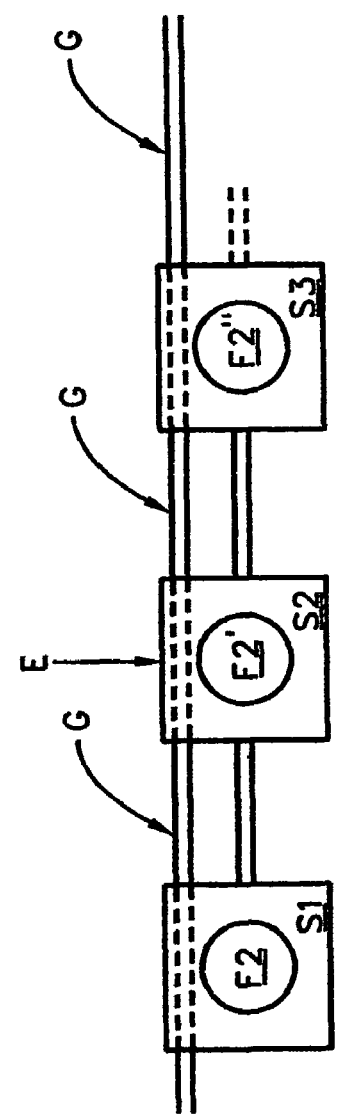

FIGS. 6a1–6a3 demonstate various systems for controling spot size of a beam of electromagnetic radiation which impinges on a sample surface. FIG. 6c demonstrates an array of slidably mounted focusing elements which provide different focal lengths, and which can be sequentially positioned in the path of a beam of electromagnetic radiation. As regards FIG. 6a1, there is shown means for providing Focusing (F1) and (F2) before and after a Sample (MS) respectively. FIGS. 6b and 6c show that, for the (F2) case, a sequence of different Focusing Elements (F2) (F2') and (F2"). A similar sequence applies for the (F1) (F1') and (F1") Focusing Elements, which in FIGS. 6b and 6c are located behind (F2) (F2') and (F2") in said Figures. Note FIG. 6a1 indicates (S1) (S2) or (S3) can be entered into the path of the Beam (E) by a sliding motion out of the page. Said (S1) (S2) and (S3) correspond the (S1) (S2) and (S3) of FIGS. 6b and 6c. FIG. 6a3 shows (S1) (S2) and (S3) oriented to be slidable in the plane of the page. FIG. 6a2 shows that Focusing Elements (F1) and (F2) can be moved along the locus of the electromagnetic beam (E) to change Focus.

Figure 7A:
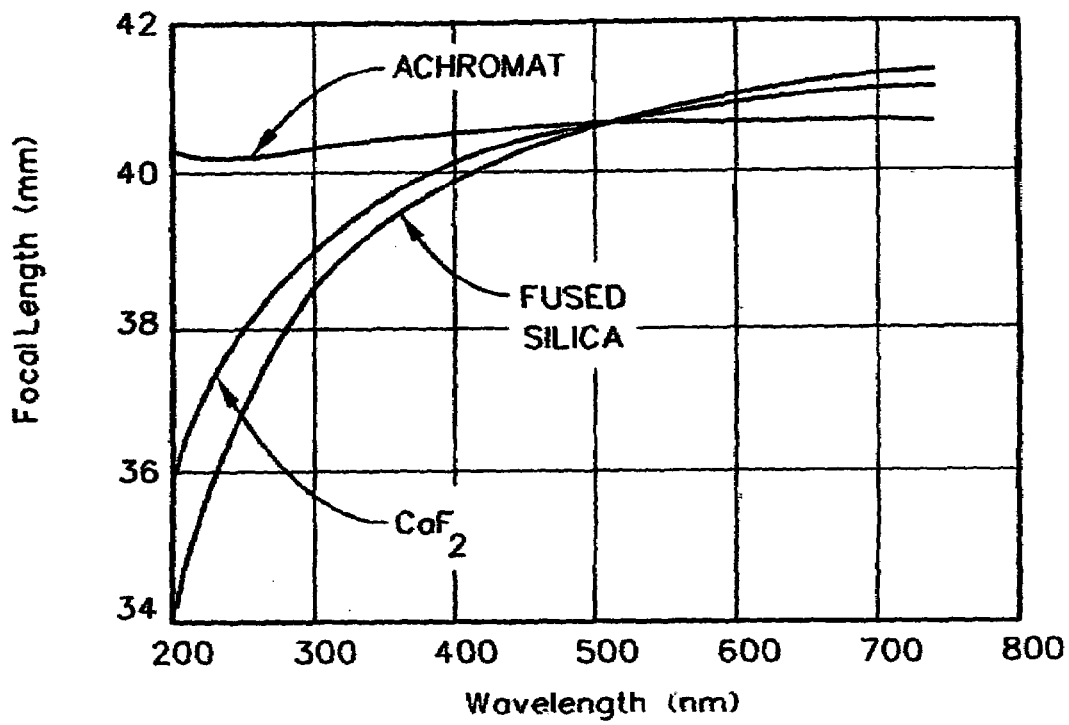
FIGS. 7a and 7b show Focal length variation as a function of wavelength for lenses which are achromatic, and fabricated from fused silica and CaF2.
Figure 7B:
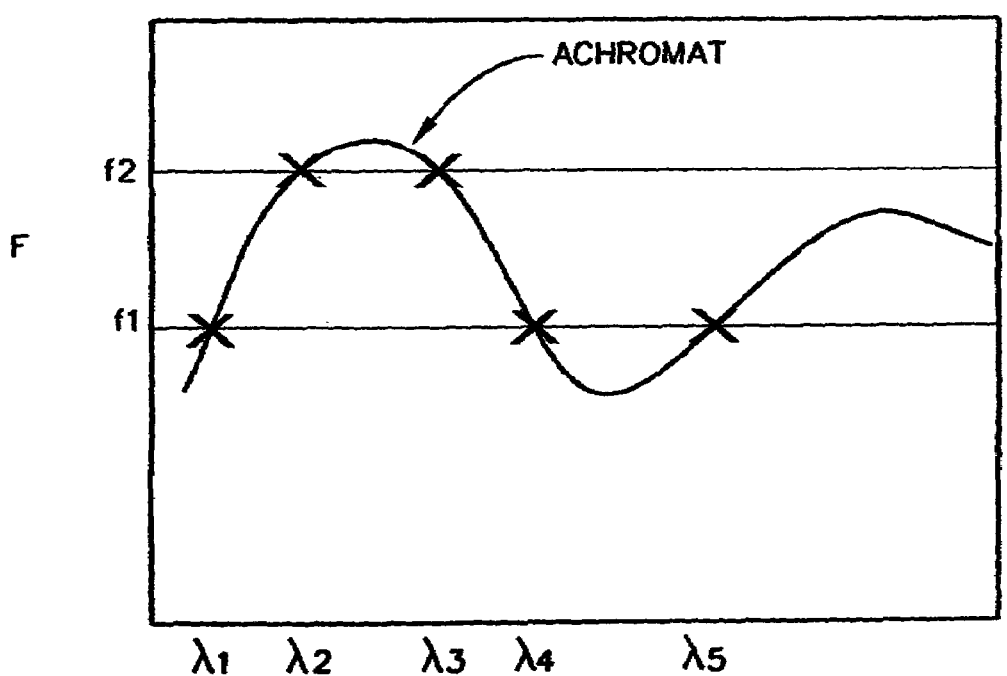

For insight, FIGS. 7a and 7b are included to show Focal length variation as a function of wavelength for lenses which are achromatic, and fabricated from fused silica and CaF2. FIG. 7b also shows that an achromat can have the same Focal Length at multiple Wavelengths.

Figure 7C:
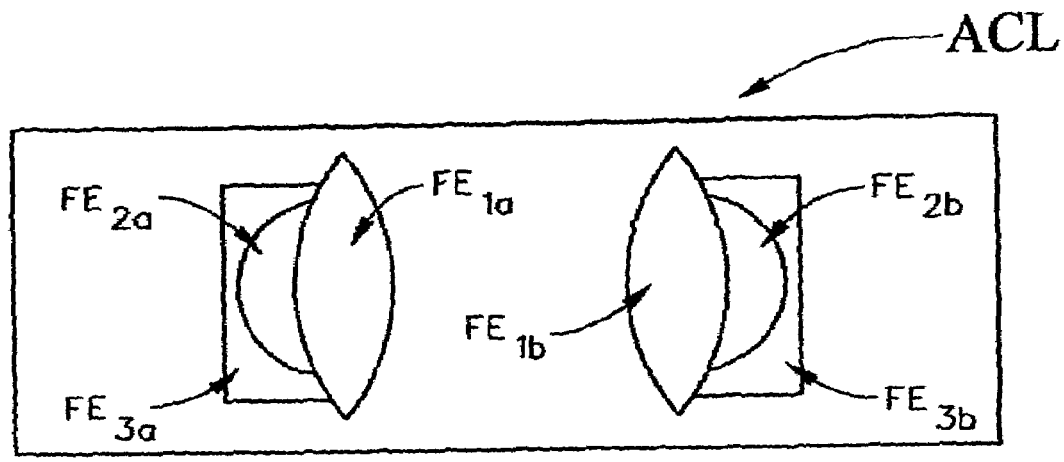

FIG. 7c shows a spot size of a beam of electromagnetic radiation which impinges on a sample surface for the achromatic, fused silica and CaF2 lenses of FIG. 7a. It should be noted that even the achromat Spot Size changes with Wavelength, which can be compensated by a focusing or d-focusing using a system such as shown in FIGS. 6a1–6a3.

Figure 7D:
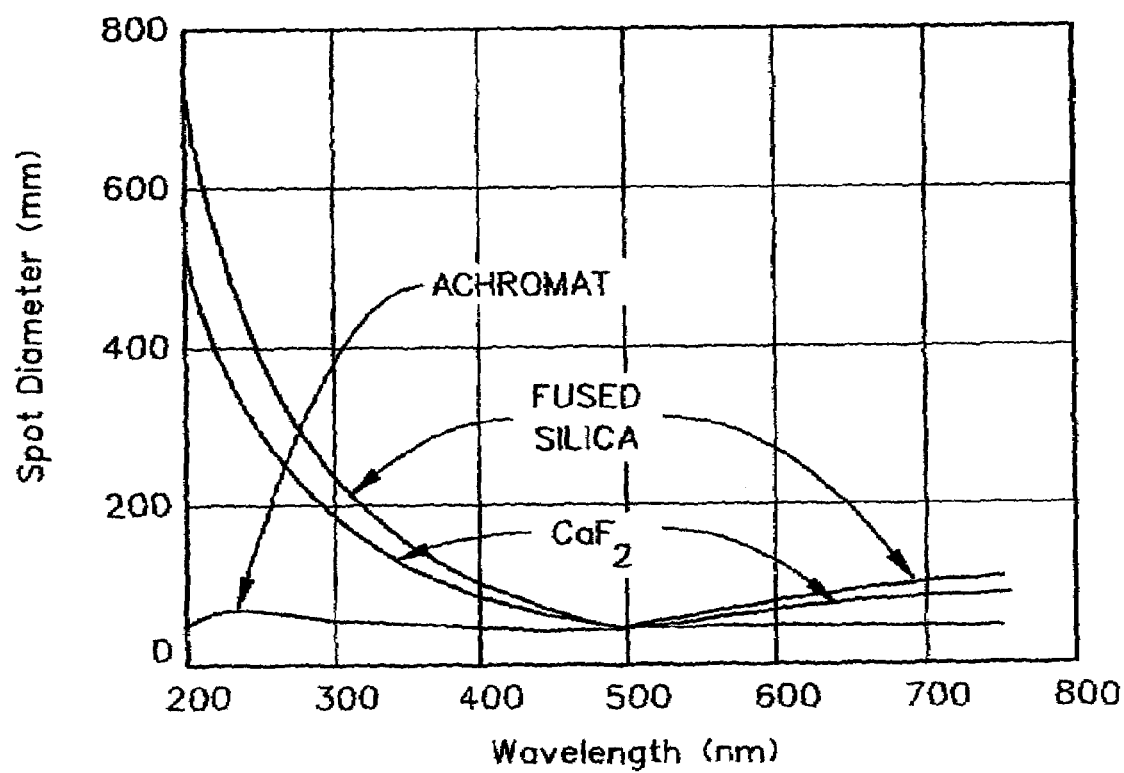
FIG. 7d demonstrates representative construction of an achromatic lens.

FIG. 7d demonstrates non-limiting construction of an achromatic lens (ACL), showing the construction comprises a dual quasi-achromatic multi-element lens with an element sequence of:
  (Diverging(D)) (element FE3a);
  (Converging(C)) (element FE1a);
  (Converging(C)) (element FE1b);
  (Diverging(D)) (element FE3b);

wherein elements FE2a and FE2b typically being void. Note that one, or both, of the two quasi-achromatic multi-element lens shown can be reversed left to right, (ie. replaced with a vertical mirror image), and remain within the scope of the present invention. Multi-element lenses which comprise elements made of different materials allow essentially the same, but not exactly the same, focal length and Spot Size to be achieved over a wide wavelength range are thus possible. Other embodiments are also possible. And FIGS. 8a–8g demonstrate various realizations of lenses which have Fluid Filled Cavities (FFC) present within Rigid Lens Elements (RLE).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for investigating a sample sequentially comprising a source of electromagnetic radiation, variable means for effecting focus or defocus of a beam of electromagnetic radiation provided by said source of electromagnetic radiation, a stage for supporting a sample, and a detector;

said source of electromagnetic radiation being spectroscopic and said variable means for effecting focus or defocus thereof being programmable to functionally correlate a specific degree of focus or defocus with each wavelength;

such that in use an electromagnetic beam is provided by said source of electromagnetic radiation and is caused to pass through said means for effecting focus or defocus thereof which applies focus or defocus thereto such that a desired spot size is achieved on said sample, then reflects from said sample and enters said detector.

2. A system as in claim 1, which further comprises a monochromator to select specific wavelengths and in which said means for effecting focus or defocus is programmable to functionally correlate a specific degree of focus or defocus with each monochromator selected wavelength.

3. A system as in claim 1, in which the detector comprises a multiplicity of detector elements and which further comprises a dispersive element positioned to receive electromagnetic radiation reflected from a sample and provide different wavelengths to different detector elements, said detector and means for effecting focus or defocus being functionally correlated such that data is accepted from a detector element only when a specific degree of focus or defocus is appropriate for the wavelength received thereby.

4. A system as in claim 1 in which the means for effecting focus or defocus comprises at least one cavity filled with a flowable material.

5. A system as in claim 4 in which the flowable material is selected from the group consisting of:
gas;
powder;
fluid;
liquid;
water base liquid;
oil base liquid.

6. A system as in claim 4 in which said at least one cavity has a geometry characterized by comprising at least one selection from the group consisting of:
at least one concave side at an interface between an effective element and a cavity boundary;
at least one convex side at an interface between an effective element and a cavity boundary;
at least one flat side at an interface between an effective element and a cavity boundary;
two concave sides at an interfaces between an effective element and a cavity boundaries;
two convex sides at an interfaces between an effective element and a cavity boundaries;
two flat sides at an interfaces between an effective element and a cavity boundaries;
one concave side and one convex interface between an effective element and a cavity boundaries;
one concave side and one flat interface between an effective element and a cavity boundaries.

7. A system as in claim 1 in which the means for effecting focus or defocus comprises a lens system selected from the group consisting of:
a) a sequential combination of a bi-convex element and a bi-concave element;
b) a sequential combination of a bi-concave element and a bi-convex element;
c) a sequential combination of a bi-convex element and a plano-concave element with said concave side of said plano-concave element adjacent to said bi-convex element;
d) a sequential combination of a bi-convex element and a plano-concave element with said essentially flat side of said plano-concave element being adjacent to said bi-convex element;
e) a sequential combination of a plano-concave element and a bi-convex element with said essentially flat side of said plano-concave element adjacent to said bi-concave element;
f) a sequential combination of a plano-concave element and bi-convex element with said concave side of said plano-concave element adjacent to said bi-convex element;
g) a sequential combination of a plano-convex element and a bi-concave element with said essentially flat side of said plano-convex element adjacent to said bi-concave element;
h) a sequential combination of a bi-concave element with a plano-convex element with said convex side of said plano-convex element adjacent to said bi-concave element;
i) a sequential combination of a piano-concave element and a plano-convex element with the essentially flat side of said plano-concave element being adjacent to the convex side of the plano-convex element;
j) a sequential combination of a plano-concave element and a plano-convex element with the essentially flat side of said planoconcave element being adjacent to the convex side of said plano-convex element;
k) a sequential combination of a plano-convex element and a plano-concave element with the essentially flat side of said plano-convex element and the essentially flat side of said plano-concave element being adjacent to one another;
l) a sequential combination of a plano-concave element and a plano-convex element with the concave side of said plano-concave element being adjacent to the convex side of the plano-convex element;
m) a sequential combination of a plano-convex element and a bi-concave element with said convex side of said plano-convex element adjacent to said bi-concave element;
n) a sequential combination of a bi-concave element and a plano-convex element with said essentially flat side of said plano-convex element adjacent to said bi-concave element;
o) a sequential combination of a plano-convex element and a plano-concave element with said convex side of said plano-convex element adjacent to the concave side of the plano-concave element;
p) a sequential combination of a plano-concave element and a plano-convex element with said essentially flat side of said plano-convex element being adjacent to the essentially flat side of the plano-concave element;
q) a sequential combination of a plano-convex element and a plano-concave element with said convex side of said plano-convex element being adjacent to the essentially flat side of the plano-concave element; and
r) a sequential combination of a plano-concave element with a plano-convex element with the essentially flat side of said plano-convex element being adjacent to the concave side of said plano-concave element;
s) in either order, a sequential combination of
a converging element which is characterized as a selection from the group consisting of:
a bi-convex;
a plano-convex with an essentially flat side;
and a diverging element which is characterized as a selection from the group consisting of:
a bi-concave lens element;
a plano-concave with an essentially flat side;
t) a sequential combination of three elements.

8. A system for investigating a sample as in claim 1 in which said variable means for effecting focus or defocus of a beam of electromagnetic radiation provided by said source of electromagnetic radiation is substantially achromatic.

9. A system for investigating a sample sequentially comprising a spectroscopic source of electromagnetic radiation, a monochromator, variable means for effecting focus or defocus of a beam of electromagnetic radiation provided by said source of electromagnetic radiation, a stage for supporting a sample, and a detector;

said variable means for effecting focus or defocus thereof being programmable to functionally correlate a specific degree of focus or defocus with each wavelength;

such that in use a spectroscopic beam of electromagnetic beam is provided by said source of electromagnetic radiation, said monochrometer selects a specific wavelength, and said means for effecting focus or defocus thereof applies focus or defocus thereto as a function of monochromator selected wavelength, such that a desired spot size is achieved on said sample, then reflects from said sample and enters said detector.

10. A system as in claim 9 in which the means for effecting focus or defocus comprises at least one cavity filled with a flowable material.

11. A system as in claim 10 in which the flowable material is selected from the group consisting of:
gas;
powder;
fluid;
liquid;
water base liquid;
oil base liquid.

12. A system as in claim 10 in which said at least one cavity has a geometry characterized by comprising at least one selection from the group consisting of:
at least one concave side at an interface between an effective element and a cavity boundary;
at least one convex side at an interface between an effective element and a cavity boundary;
at least one flat side at an interface between an effective element and a cavity boundary;
two concave sides at an interfaces between an effective element and a cavity boundaries;
two convex sides at an interfaces between an effective element and a cavity boundaries;
two flat sides at an interfaces between an effective element and a cavity boundaries;
one concave side and one convex interface between an effective element and a cavity boundaries;
one concave side and one flat interface between an effective element and a cavity boundaries.

13. A system as in claim 9 in which the means for effecting focus or defocus comprises a lens system selected from the group consisting of:
a) a sequential combination of a bi-convex element and a bi-concave element;
b) a sequential combination of a bi-concave element and a bi-convex element;
c) a sequential combination of a bi-convex element and a plano-concave element with said concave side of said plano-concave element adjacent to said bi-convex element;
d) a sequential combination of a bi-convex element and a plano-concave element with said essentially flat side of said plano-concave element being adjacent to said bi-convex element;
e) a sequential combination of a plano-concave element and a bi-convex element with said essentially flat side of said plano-concave element adjacent to said bi-concave element;
f) a sequential combination of a plano-concave element and bi-convex element with said concave side of said plano-concave element adjacent to said bi-convex element;

g) a sequential combination of a plano-convex element and a bi-concave element with said essentially flat side of said plano-convex element adjacent to said bi-concave element;
h) a sequential combination of a bi-concave element with a plano-convex element with said convex side of said plano-convex element adjacent to said bi-concave element;
i) a sequential combination of a plano-concave element and a plano-convex element with the essentially flat side of said plano-concave element being adjacent to the convex side of the plano-convex element;
j) a sequential combination of a plano-concave element and a plano-convex element with the essentially flat side of said planoconcave element being adjacent to the convex side of said plano-convex element;
k) a sequential combination of a plano-convex element and a plano-concave element with the essentially flat side of said plano-convex element and the essentially flat side of said plano-concave element being adjacent to one another;
l) a sequential combination of a plano-concave element and a plano-convex element with the concave side of said plano-concave element being adjacent to the convex side of the plano-convex element;
m) a sequential combination of a plano-convex element and a bi-concave element with said convex side of said plano-convex element adjacent to said bi-concave element;
n) a sequential combination of a bi-concave element and a plano-convex element with said essentially flat side of said plano-convex element adjacent to said bi-concave element;
o) a sequential combination of a plano-convex element and a plano-concave element with said convex side of said plano-convex element adjacent to the concave side of the plano-concave element;
p) a sequential combination of a plano-concave element and a plano-convex element with said essentially flat side of said plano-convex element being adjacent to the essentially flat side of the plano-concave element;
q) a sequential combination of a plano-convex element and a plano-concave element with said convex side of said plano-convex element being adjacent to the essentially flat side of the plano-concave element; and
r) a sequential combination of a plano-concave element with a plano-convex element with the essentially flat side of said plano-convex element being adjacent to the concave side of said plano-concave element;
s) in either order, a sequential combination of
a converging element which is characterized as a selection from the group consisting of:
a bi-convex;
a plano-convex with an essentially flat side;
and a diverging element which is characterized as a selection from the group consisting of:
a bi-concave lens element;
a plano-concave with an essentially flat side;
t) a sequential combination of three elements.

14. A method of investigating a specifically defined area on a sample comprising the steps of:
a) providing a system for investigating a sample comprising a spectroscopic source of electromagnetic radiation, a stage for supporting a sample and a detector, there being a sample positioned on said stage for supporting a sample, said system further comprising a two-dimensional detector array which comprises a multiplicity of detector elements, said two-dimensional detector array being positioned such that different detector elements receive electromagnetic radiation reflected from different locations on said sample;

said system further comprising a variable means for effecting focus or defocus of a beam of electromagnetic radiation onto said sample, and a monochromator, said means for effecting focus or defocus of a beam of electromagnetic radiation onto said sample and monochromator being functionally correlated such that at any selected wavelength the spot size of said electromagnetic beam on said sample is maintained essentially constant;

such that in use a spectroscopic beam of electromagnetic beam is provided by said source of electromagnetic radiation and said spectroscopic beam then being reflected from said sample and enter said two dimensional detector;

b) said method being characterized in that data from specific groups of detector elements are analyzed separately from data detected by other detector elements.

15. A method of investigating a specifically defined area on a sample comprising the steps of:
   a) providing a system for investigating a sample comprising a spectroscopic source of electromagnetic radiation, a stage for supporting a sample and a detector, said system further comprising a monochromator and variable means for effecting focus or defocus of a beam of electromagnetic radiation provided by said source of electromagnetic radiation, at the location where said beam impinges on a surface of a sample positioned upon said stage, the purpose being, at a sequential plurality of wavelengths, to enable controlling spot beam size thereat;
   b) placing a sample comprising a non-uniform surface on said stage for supporting a sample and determining a desired beam spot size at the location at which said beam impinges on said sample;
   c) causing a beam of electromagnetic radiation from said source of electromagnetic radiation which is of a wavelength selected by said monochromator, to impinge on said surface of said sample;
   d) for each of a sequence of wavelengths adjusting said variable means for effecting focus or defocus of a beam of electromagnetic radiation to provide a beam spot size at the location whereat said electromagnetic beam impinges on said non-uniform sample surface;

with the effect being that a spot of constant size on the surface of said sample is investigated at a plurality of wavelengths.

16. A method as in claim 15 in which said detector is selected to be a two dimensional array comprising a multiplicity of detector elements.

17. A method as in claim 16 in which data is acquired from a subset of the multiplicity of detector elements.

18. A method as in claim 15, in which the step of providing a system further comprises providing a polarizer and analyzer ahead of and after said sample such that said system is an ellipsometer or polarimeter, said method further comprising determining ellipsometric PSI and ellipsometric DELTA for said sample by a technique which compensates for birefringence of said variable means for effecting focus or defocus of a beam of electromagnetic radiation provided by said source of electromagnetic radiation, at the location where said beam impinges on a surface of a sample.

19. A method of investigating desired features of a sample surface comprising the steps of:
   a) providing a system for investigating a sample comprising a source of electromagnetic radiation, a stage for supporting a sample and a two dimensional multi-element detector, said system further comprising variable means for effecting focus or defocus of a beam of electromagnetic radiation provided by said source of electromagnetic radiation, at the location where said beam impinges on a surface of a sample positioned upon said stage, the purpose being to enable controlling spot beam size thereat, said system further comprising a polarizer and analyzer ahead of and after said sample, respectively, such that said system is an ellipsometer or polarimeter;
   b) placing a sample on said stage for supporting a sample;
   c) causing a beam of electromagnetic radiation from said source of electromagnetic radiation to impinge on a surface of said sample;
   d) adjusting said variable means for effecting focus or defocus of a beam of electromagnetic radiation to provide a beam spot size at the location whereat said electromagnetic beam impinges on said sample surface;

such that electromagnetic radiation from said spot on said surface of said sample is reflected into said two dimensional multi-element detector; and selecting a subset of said detector elements in said detector for which to secure data, and analyzing said secured data;

said method further comprising determining ellipsometric PSI and ellipsometric DELTA for said sample by a technique which compensates for birefringence of said variable means for effecting focus or defocus of a beam of electromagnetic radiation provided by said source of electromagnetic radiation, at the location where said beam impinges on a surface of a sample.

20. A method of investigating a specifically defined area on a sample comprising the steps of:
   a) providing a system for investigating a sample which sequentially comprises a spectroscopic source of electromagnetic radiation, a monochromator, variable means for effecting focus or defocus of a beam of electromagnetic radiation provided by said source of electromagnetic radiation, a stage for supporting a sample, and a detector;

such that in use an electromagnetic beam is provided by said source of electromagnetic radiation and is caused to pass through said monochromator and means for effecting focus or defocus thereof, interact with said sample and enter said detector;

repeating steps b through d a multiplicity of times:
   b) causing said spectroscopic source to provide a beam of electromagnetism and direct it into said monochromator, which monochromator passes a desired wavelength in said spectroscopic beam and directs it into said variable means for effecting focus or defocus of a beam of electromagnetic radiation;
   c) for each wavelength causing said variable means for effecting focus or defocus of a beam of electromagnetic radiation to provide a predetermined defocused spot size on said sample, such that said beam of electromagnetism interacts with said sample, and enters said detector; and
   d) for each wavelength causing said detector to acquire data which corresponds to a predetermined spot size which is the same size at each wavelength;

with the effect being that a spot on the surface of said sample is investigated at a plurality of wavelengths.

21. A method as in claim, 20, in which the variable means for effecting focus or defocus of a beam of electromagnetic radiation is substantially achromatic and in which the variable means for providing a predetermined defocused spot size on said sample is set the same for each wavelength.

22. A method as in claim 21 in which a three dimensional data set is developed corresponding to two dimensional surface data at each of a multiplicity of wavelengths, at least one of said two dimensional data sets corresponding to different electromagnetic beam spot size on the sample surface than does another of said two dimensional data sets.

23. A method as in claim, 20, in which the variable means for effecting focus or defocus of a beam of electromagnetic radiation is adjusted differently for at least two wavelengths.

24. A method as in claim, 20, in which the variable means for effecting focus or defocus of a beam of electromagnetic radiation is adjusted appropriately at each wavelength so that the same spot size is achieved on the sample surface at each thereof.

25. A method as in claim 24 in which a three dimensional data set is developed corresponding to a multiplicity of two dimensional surface data sets at each of a multiplicity of wavelengths, each two dimensional surface data set corresponding to the same electromagnetic beam spot size on the sample surface at each thereof.

26. A method of investigating a specifically defined area on a sample comprising the steps of:
  a) providing a system for investigating a sample which sequentially comprises a spectroscopic source of electromagnetic radiation, variable means for effecting focus or defocus of a beam of electromagnetic radiation provided by said source of electromagnetic radiation, a stage for supporting a sample, and a detector;
said source of electromagnetic radiation being spectroscopic and said variable means for effecting focus or defocus thereof being programmable to functionally correlate a specific degree of focus or defocus with each wavelength; such that in use an electromagnetic beam is provided by said source of electromagnetic radiation and is caused to pass through said means for effecting focus or defocus thereof, interact with said sample and enter said detector;
repeating steps b, c and d a multiplicity of times:
  b) causing said spectroscopic source to provide a beam of electromagnetism and direct it into said variable means for effecting focus or defocus of a beam of electromagnetic radiation;
  c) causing said variable means for effecting focus or defocus of a beam of electromagnetic radiation to provide a predetermined defocused spot size on said sample, such that said beam of electromagnetism interacts with said sample, and enters said detector; and
  d) for each:
    row or column;
in a two dimensional array corresponding to the surface of said sample, causing said detector to acquire data corresponding at a multiplicity of:
    column or row points, respectively;
and a multiplicity of wavelengths;
with the effect being that a three dimensional data set is developed corresponding to two dimensional surface data at each of a multiplicity of wavelengths.

27. A method as in claim 26 wherein said variable means for effecting focus or defocus of a beam of electromagnetic radiation to provide a predetermined spot size on said sample is adjusted differently at least two different wavelengths.

28. A method as in claim 26 wherein said variable means for effecting focus or defocus of a beam of electromagnetic radiation to provide a predetermined spot size on said sample is substantially achromatic and is adjusted at one wavelength and not changed thereafter.

29. A method of investigating a specifically defined area on a sample comprising the steps of:
  a) providing a system for investigating a sample sequentially comprising a source of electromagnetic radiation, a substantially achromatic variable means for effecting focus or defocus of a beam of electromagnetic radiation provided by said source of electromagnetic radiation, a stage for supporting a sample, and a detector;
said source of electromagnetic radiation being spectroscopic and said variable means for effecting focus or defocus thereof being programmable to functionally correlate a specific degree of focus or defocus with each wavelength; such that in use an electromagnetic beam is provided by said source of electromagnetic radiation and is caused to pass through said means for effecting focus or defocus thereof which applies focus or defocus thereto such that a desired spot size is achieved on said sample, then reflects from said sample and enters said detector;
  b) placing a sample comprising a non-uniform surface on said stage for supporting a sample and determining a desired beam spot size at the location at which said beam impinges on said sample;
  c) causing a spectroscopic beam of electromagnetic radiation from said source of electromagnetic radiation to impinge on said surface of said sample;
  d) adjusting said substantially achromatic variable means for effecting focus or defocus of a beam of electromagnetic radiation to provide a beam spot size at the location whereat said electromagnetic beam impinges on said non-uniform sample surface;
with the effect being that a spot of essentially constant size on the surface of said sample is investigated at a plurality of wavelengths.

* * * * *